US012781213B2

(12) United States Patent
Shirai et al.

(10) Patent No.: US 12,781,213 B2
(45) Date of Patent: Nov. 3, 2026

(54) **METHOD OF PRODUCING UNSATURATED HYDROCARBON COMPOUNDS WITH MUTATED FERULIC ACID FROM *SACCHAROMYCES***

(71) Applicants: RIKEN, Wako (JP); ZEON CORPORATION, Tokyo (JP); THE Yokohama Rubber Co., Ltd., Tokyo (JP)

(72) Inventors: Tomokazu Shirai, Wako (JP); Yutaro Mori, Wako (JP); Kazuhiro Takahashi, Tokyo (JP); Yayoi Akahori, Hiratsuka (JP)

(73) Assignees: RIKEN, Saitama (JP); ZEON CORPORATION, Tokyo (JP); THE YOKOHAMA RUBBER CO., LTD., Tokyo (JP)

( * ) Notice: Subject to any disclaimer, the term of this patent is extended or adjusted under 35 U.S.C. 154(b) by 688 days.

(21) Appl. No.: 17/762,184

(22) PCT Filed: Sep. 18, 2020

(86) PCT No.: PCT/JP2020/035442

§ 371 (c)(1),
(2) Date: Mar. 21, 2022

(87) PCT Pub. No.: WO2021/054441

PCT Pub. Date: Mar. 25, 2021

(65) Prior Publication Data

US 2023/0068606 A1 Mar. 2, 2023

(30) Foreign Application Priority Data

Sep. 20, 2019 (JP) ................................ 2019-172227

(51) Int. Cl.
*C12N 9/88* (2006.01)
*C12N 15/63* (2006.01)
*C12P 5/02* (2006.01)

(52) U.S. Cl.
CPC ............... *C12N 9/88* (2013.01); *C12N 15/63* (2013.01); *C12P 5/02* (2013.01); *C12Y 401/01* (2013.01)

(58) Field of Classification Search
None
See application file for complete search history.

(56) References Cited

FOREIGN PATENT DOCUMENTS

| | | | | | |
|---|---|---|---|---|---|
| JP | 2014-30376 | A | | 2/2014 | |
| JP | 2015-228804 | A | | 12/2015 | |
| JP | 2019-500022 | A | | 1/2019 | |
| WO | WO-2016050842 | A1 | * | 4/2016 | ............. C12N 15/52 |
| WO | WO-2017168161 | A1 | * | 10/2017 | ............. C12N 15/52 |
| WO | 2017/191239 | A1 | | 11/2017 | |
| WO | 2019/022083 | A1 | | 1/2019 | |

OTHER PUBLICATIONS

Jul. 11, 2024 Office Action issued in Japanese Patent Application No. 2021-546978.

Database: UniProtKB [online], Accession: H0GTK3,"Ferulic acid decarboxylase 1," [searched on Jul. 1, 2024], Feb. 22, 2012, the Internet, <URL:https://www.uniprot.org/uniprotkb/H0GTK3/entry>.

Database: UniProtKB [online], Accession: J8TRN5, "Ferulic acid decarboxylase 1," [searched for Jul. 1, 2024], Oct. 31, 2012, the Internet, <URL:https://www.uniprot.org/uniprotkb/J8TRN5/entry>.

Database: UniProtKB [online], Accession: A0A0L8RE03, "Ferulic acid decarboxylase 1," [searched on Jul. 1, 2024], Nov. 11, 2015, the Internet, <URL:https://www.uniprot.org/uniprotkb/A0A0L8RE03/entry>.

Mar. 15, 2022 International Preliminary Report on Patentability issued in International Patent Application No. PCT/JP2020/035442.

Payne, Karl A. P. et al., "New Cofactor Supports Alpha, Beta-Unsaturated Acid Decarboxylation via 1, 3-Dipolar Cycloaddition," Nature, vol. 522, Issue 7557, pp. 497-501, Jun. 25, 2015.

Bhuiya Mohammad Wadud et al., "Structure and Mechanism of Ferulic Acid Decarboxylase (FDC1) From *Saccharomyces cerevisiae,*" Applied and Environmental Microbiology, vol. 81, No. 12, pp. 4126-4223, 2015.

Nov. 17, 2020 International Search Report issued in International Patent Application No. PCT/JP2020/035442.

* cited by examiner

*Primary Examiner* — Hope A Robinson
(74) *Attorney, Agent, or Firm* — Oliff PLC

(57) ABSTRACT

Wild-type ferulic acid decarboxylase obtained from *Saccharomyces* has high catalytic activity for the production of unsaturated hydrocarbon compounds. Further, in the ferulic acid decarboxylase, substitution of the amino acid at position 398 of SEQ ID NO: 2 with glutamine, methionine, asparagine, phenylalanine, histidine, or threonine improves the catalytic activity, making it possible to provide a method capable of producing an unsaturated hydrocarbon compound like butadiene with high productivity, and an enzyme used in the method.

6 Claims, No Drawings

Specification includes a Sequence Listing.

SEQUENCE LISTING

```
<160> NUMBER OF SEQ ID NOS: 7

<210> SEQ ID NO 1
<211> LENGTH: 1512
<212> TYPE: DNA
<213> ORGANISM: Saccharomyces cerevisiae
<220> FEATURE:
<221> NAME/KEY: CDS
<222> LOCATION: (1)..(1512)
<223> OTHER INFORMATION: Ferulic acid decarboxylase

<400> SEQUENCE: 1

atg agg aag cta aat cca gct tta gaa ttt aga gac ttt atc cag gtc       48
Met Arg Lys Leu Asn Pro Ala Leu Glu Phe Arg Asp Phe Ile Gln Val
1               5                   10                  15

tta aaa gat gaa gat gac tta atc gaa att acc gaa gag att gat cca       96
Leu Lys Asp Glu Asp Asp Leu Ile Glu Ile Thr Glu Glu Ile Asp Pro
            20                  25                  30

aat ctc gaa gta ggt gca att atg agg aag gcc tat gaa tcc cac tta      144
Asn Leu Glu Val Gly Ala Ile Met Arg Lys Ala Tyr Glu Ser His Leu
        35                  40                  45

cca gcc ccg tta ttt aaa aat ctc aaa ggt gct tcg aag gat ctt ttc      192
Pro Ala Pro Leu Phe Lys Asn Leu Lys Gly Ala Ser Lys Asp Leu Phe
    50                  55                  60

agc att tta ggt tgc cca gcc ggt ttg aga agt aag gag aaa gga gat      240
Ser Ile Leu Gly Cys Pro Ala Gly Leu Arg Ser Lys Glu Lys Gly Asp
65                  70                  75                  80

cat ggt aga att gcc cat cat ctg ggg ctc gac cca aaa aca act atc      288
His Gly Arg Ile Ala His His Leu Gly Leu Asp Pro Lys Thr Thr Ile
                85                  90                  95

aag gaa atc ata gat tat ttg ctg gag tgt aag gag aag gaa cct ctc      336
Lys Glu Ile Ile Asp Tyr Leu Leu Glu Cys Lys Glu Lys Glu Pro Leu
            100                 105                 110

ccc cca atc act gtt cct gtg tca tct gca cct tgt aaa aca cat ata      384
Pro Pro Ile Thr Val Pro Val Ser Ser Ala Pro Cys Lys Thr His Ile
```

-continued

```
        115                 120                 125

ctt tct gaa gaa aaa ata cat cta caa agc ctg cca aca cca tat cta      432
Leu Ser Glu Glu Lys Ile His Leu Gln Ser Leu Pro Thr Pro Tyr Leu
    130                 135                 140

cat gtt tca gac ggt ggc aag tac tta caa acg tac gga atg tgg att      480
His Val Ser Asp Gly Gly Lys Tyr Leu Gln Thr Tyr Gly Met Trp Ile
145                 150                 155                 160

ctt caa act cca gat aaa aaa tgg act aat tgg tca att gct aga ggt      528
Leu Gln Thr Pro Asp Lys Lys Trp Thr Asn Trp Ser Ile Ala Arg Gly
                165                 170                 175

atg gtt gta gat gac aag cat atc act ggt ctg gta att aaa cca caa      576
Met Val Val Asp Asp Lys His Ile Thr Gly Leu Val Ile Lys Pro Gln
            180                 185                 190

cat att aga caa att gct gac tct tgg gca gca att gga aaa gca aat      624
His Ile Arg Gln Ile Ala Asp Ser Trp Ala Ala Ile Gly Lys Ala Asn
        195                 200                 205

gaa att cct ttc gcg tta tgt ttt ggc gtt ccc cca gca gct att tta      672
Glu Ile Pro Phe Ala Leu Cys Phe Gly Val Pro Pro Ala Ala Ile Leu
    210                 215                 220

gtt agt tcc atg cca att cct gaa ggt gtt tct gaa tcg gat tat gtt      720
Val Ser Ser Met Pro Ile Pro Glu Gly Val Ser Glu Ser Asp Tyr Val
225                 230                 235                 240

ggc gca atc ttg ggt gag tcg gtt cca gta gta aaa tgt gag acc aac      768
Gly Ala Ile Leu Gly Glu Ser Val Pro Val Val Lys Cys Glu Thr Asn
                245                 250                 255

gat tta atg gtt cct gca acg agt gag atg gta ttt gag ggt act ttg      816
Asp Leu Met Val Pro Ala Thr Ser Glu Met Val Phe Glu Gly Thr Leu
            260                 265                 270

tcc tta aca gat aca cat ctg gaa ggc cca ttt ggt gag atg cat gga      864
Ser Leu Thr Asp Thr His Leu Glu Gly Pro Phe Gly Glu Met His Gly
        275                 280                 285

tat gtt ttc aaa agc caa ggt cat cct tgt cca ttg tac act gtc aag      912
Tyr Val Phe Lys Ser Gln Gly His Pro Cys Pro Leu Tyr Thr Val Lys
    290                 295                 300

gct atg agt tac aga gac aat gct att cta cct gtt tcg aac ccc ggt      960
Ala Met Ser Tyr Arg Asp Asn Ala Ile Leu Pro Val Ser Asn Pro Gly
305                 310                 315                 320

ctt tgt acg gat gag aca cat acc ttg att ggt tca cta gtg gct act     1008
Leu Cys Thr Asp Glu Thr His Thr Leu Ile Gly Ser Leu Val Ala Thr
                325                 330                 335

gag gcc aag gag ctg gct att gaa tct ggc ttg cca att ctg gat gcc     1056
Glu Ala Lys Glu Leu Ala Ile Glu Ser Gly Leu Pro Ile Leu Asp Ala
            340                 345                 350

ttt atg cct tat gag gct cag gct ctt tgg ctt atc tta aag gtg gat     1104
Phe Met Pro Tyr Glu Ala Gln Ala Leu Trp Leu Ile Leu Lys Val Asp
        355                 360                 365

ttg aaa ggg ctg caa gca ttg aag aca acg cct gaa gaa ttt tgt aag     1152
Leu Lys Gly Leu Gln Ala Leu Lys Thr Thr Pro Glu Glu Phe Cys Lys
    370                 375                 380

aag gta ggt gat att tac ttt agg aca aaa gtt ggt ttt ata gtc cat     1200
Lys Val Gly Asp Ile Tyr Phe Arg Thr Lys Val Gly Phe Ile Val His
385                 390                 395                 400

gaa ata att ttg gtg gca gat gat atc gac ata ttt aac ttc aaa gaa     1248
Glu Ile Ile Leu Val Ala Asp Asp Ile Asp Ile Phe Asn Phe Lys Glu
                405                 410                 415

gtc atc tgg gcc tac gtt aca aga cat aca cct gtt gca gat cag atg     1296
Val Ile Trp Ala Tyr Val Thr Arg His Thr Pro Val Ala Asp Gln Met
            420                 425                 430

gct ttt gat gat gtc act tct ttt cct ttg gct ccc ttt gtt tcg cag     1344
```

-continued

```
Ala Phe Asp Asp Val Thr Ser Phe Pro Leu Ala Pro Phe Val Ser Gln
        435                 440                 445

tca tcc aga agt aag act atg aaa ggt gga aag tgc gtt act aat tgc     1392
Ser Ser Arg Ser Lys Thr Met Lys Gly Gly Lys Cys Val Thr Asn Cys
    450                 455                 460

ata ttt aga cag caa tat gag cgc agt ttt gac tac ata act tgt aat     1440
Ile Phe Arg Gln Gln Tyr Glu Arg Ser Phe Asp Tyr Ile Thr Cys Asn
465                 470                 475                 480

ttt gaa aag gga tat cca aaa gga tta gtt gac aaa gta aat gaa aat     1488
Phe Glu Lys Gly Tyr Pro Lys Gly Leu Val Asp Lys Val Asn Glu Asn
                485                 490                 495

tgg aaa agg tac gga tat aaa taa                                     1512
Trp Lys Arg Tyr Gly Tyr Lys
            500


<210> SEQ ID NO 2
<211> LENGTH: 503
<212> TYPE: PRT
<213> ORGANISM: Saccharomyces cerevisiae

<400> SEQUENCE: 2

Met Arg Lys Leu Asn Pro Ala Leu Glu Phe Arg Asp Phe Ile Gln Val
1               5                   10                  15

Leu Lys Asp Glu Asp Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
            180                 185                 190

His Ile Arg Gln Ile Ala Asp Ser Trp Ala Ala Ile Gly Lys Ala Asn
        195                 200                 205

Glu Ile Pro Phe Ala Leu Cys Phe Gly Val Pro Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Val Lys Cys Glu Thr Asn
                245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
```

```
        275                 280                 285

Tyr Val Phe Lys Ser Gln Gly His Pro Cys Pro Leu Tyr Thr Val Lys
    290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500


<210> SEQ ID NO 3
<211> LENGTH: 1512
<212> TYPE: DNA
<213> ORGANISM: Artificial Sequence
<220> FEATURE:
<223> OTHER INFORMATION: Sequence codon-optimized for E.coli expression
<220> FEATURE:
<221> NAME/KEY: CDS
<222> LOCATION: (1)..(1512)

<400> SEQUENCE: 3

atg cgt aaa ctg aat ccg gca ctg gaa ttt cgt gat ttt att cag gtt       48
Met Arg Lys Leu Asn Pro Ala Leu Glu Phe Arg Asp Phe Ile Gln Val
1               5                   10                  15

ctg aaa gat gag gat gac ctg att gaa atc acc gaa gaa att gat ccg       96
Leu Lys Asp Glu Asp Asp Leu Ile Glu Ile Thr Glu Glu Ile Asp Pro
            20                  25                  30

aat ctg gaa gtt ggt gcc att atg cgt aaa gca tat gaa agc cat ctg      144
Asn Leu Glu Val Gly Ala Ile Met Arg Lys Ala Tyr Glu Ser His Leu
        35                  40                  45

cct gca ccg ctg ttt aaa aac ctg aaa ggt gca agc aaa gac ctg ttt      192
Pro Ala Pro Leu Phe Lys Asn Leu Lys Gly Ala Ser Lys Asp Leu Phe
    50                  55                  60

agc att ctg ggt tgt ccg gca ggt ctg cgt agc aaa gaa aaa ggt gat      240
Ser Ile Leu Gly Cys Pro Ala Gly Leu Arg Ser Lys Glu Lys Gly Asp
65                  70                  75                  80

cat ggt cgt att gcc cat cat ctg ggt tta gat ccg aaa acc acc atc      288
His Gly Arg Ile Ala His His Leu Gly Leu Asp Pro Lys Thr Thr Ile
```

-continued

```
                85                  90                  95

aaa gag atc atc gat tat ctg ctg gaa tgc aaa gag aaa gaa ccg ctg      336
Lys Glu Ile Ile Asp Tyr Leu Leu Glu Cys Lys Glu Lys Glu Pro Leu
            100                 105                 110

cct ccg att acc gtt ccg gtt agc agc gca ccg tgt aaa acc cat att      384
Pro Pro Ile Thr Val Pro Val Ser Ser Ala Pro Cys Lys Thr His Ile
        115                 120                 125

ctg agc gaa gaa aaa atc cat ctg cag agc ctg ccg aca ccg tat ctg      432
Leu Ser Glu Glu Lys Ile His Leu Gln Ser Leu Pro Thr Pro Tyr Leu
    130                 135                 140

cat gtt tca gat ggt ggt aaa tat ctg cag acc tat ggt atg tgg att      480
His Val Ser Asp Gly Gly Lys Tyr Leu Gln Thr Tyr Gly Met Trp Ile
145                 150                 155                 160

ctg cag aca ccg gac aaa aaa tgg acc aat tgg agc att gca cgt ggt      528
Leu Gln Thr Pro Asp Lys Lys Trp Thr Asn Trp Ser Ile Ala Arg Gly
            165                 170                 175

atg gtt gtt gat gat aaa cat att acc ggt ctg gtg att aaa ccg cag      576
Met Val Val Asp Asp Lys His Ile Thr Gly Leu Val Ile Lys Pro Gln
            180                 185                 190

cat att cgt cag att gca gat agc tgg gca gca att ggt aaa gcc aat      624
His Ile Arg Gln Ile Ala Asp Ser Trp Ala Ala Ile Gly Lys Ala Asn
        195                 200                 205

gaa att ccg ttt gca ctg tgt ttt ggt gtt ccg cct gca gca att ctg      672
Glu Ile Pro Phe Ala Leu Cys Phe Gly Val Pro Pro Ala Ala Ile Leu
    210                 215                 220

gtg agc agc atg ccg att ccg gaa ggt gtt agc gaa agc gat tat gtt      720
Val Ser Ser Met Pro Ile Pro Glu Gly Val Ser Glu Ser Asp Tyr Val
225                 230                 235                 240

ggt gcg att ctg ggt gaa agc gtt ccg gtg gtt aaa tgt gaa acc aat      768
Gly Ala Ile Leu Gly Glu Ser Val Pro Val Val Lys Cys Glu Thr Asn
            245                 250                 255

gat ctg atg gtt ccg gca acc agc gaa atg gtt ttt gaa ggc acc ctg      816
Asp Leu Met Val Pro Ala Thr Ser Glu Met Val Phe Glu Gly Thr Leu
            260                 265                 270

agc ctg acc gat aca cat ctg gaa ggt ccg ttt ggt gaa atg cat ggt      864
Ser Leu Thr Asp Thr His Leu Glu Gly Pro Phe Gly Glu Met His Gly
        275                 280                 285

tat gtg ttt aaa agc cag ggt cat ccg tgt ccg ctg tat acc gtt aaa      912
Tyr Val Phe Lys Ser Gln Gly His Pro Cys Pro Leu Tyr Thr Val Lys
    290                 295                 300

gca atg agc tat cgt gat aat gca att ctg ccg gtg agc aat ccg ggt      960
Ala Met Ser Tyr Arg Asp Asn Ala Ile Leu Pro Val Ser Asn Pro Gly
305                 310                 315                 320

ctg tgt acc gat gaa acc cat aca ctg att ggt agc ctg gtt gcc acc     1008
Leu Cys Thr Asp Glu Thr His Thr Leu Ile Gly Ser Leu Val Ala Thr
            325                 330                 335

gaa gca aaa gaa ctg gca att gaa agc ggt ctg ccg att ctg gat gca     1056
Glu Ala Lys Glu Leu Ala Ile Glu Ser Gly Leu Pro Ile Leu Asp Ala
            340                 345                 350

ttt atg ccg tat gaa gca cag gca ctg tgg ctg att ctg aaa gtt gat     1104
Phe Met Pro Tyr Glu Ala Gln Ala Leu Trp Leu Ile Leu Lys Val Asp
        355                 360                 365

ctg aaa gga ctg cag gca ctg aaa acc aca ccg gaa gaa ttt tgt aaa     1152
Leu Lys Gly Leu Gln Ala Leu Lys Thr Thr Pro Glu Glu Phe Cys Lys
    370                 375                 380

aaa gtg ggc gat atc tac ttc cgt acc aaa gtt ggt ttt atc gtg cat     1200
Lys Val Gly Asp Ile Tyr Phe Arg Thr Lys Val Gly Phe Ile Val His
385                 390                 395                 400

gaa att att ctg gtg gcc gat gat atc gac atc ttc aac ttt aaa gaa     1248
```

-continued

```
Glu Ile Ile Leu Val Ala Asp Asp Ile Asp Ile Phe Asn Phe Lys Glu
                405                 410                 415

gtg att tgg gca tac gtg acc cgt cat aca ccg gtt gca gat cag atg      1296
Val Ile Trp Ala Tyr Val Thr Arg His Thr Pro Val Ala Asp Gln Met
            420                 425                 430

gca ttt gat gat gtt acc agc ttt ccg ctg gca ccg ttt gtt agc cag      1344
Ala Phe Asp Asp Val Thr Ser Phe Pro Leu Ala Pro Phe Val Ser Gln
        435                 440                 445

agc agc cgt agc aaa aca atg aaa ggt ggc aaa tgt gtg acc aac tgt      1392
Ser Ser Arg Ser Lys Thr Met Lys Gly Gly Lys Cys Val Thr Asn Cys
    450                 455                 460

att ttt cgt cag cag tat gaa cgc agc ttc gat tat atc acc tgt aac      1440
Ile Phe Arg Gln Gln Tyr Glu Arg Ser Phe Asp Tyr Ile Thr Cys Asn
465                 470                 475                 480

ttt gaa aag ggc tat ccg aaa ggt ctg gtg gat aaa gtt aat gaa aac      1488
Phe Glu Lys Gly Tyr Pro Lys Gly Leu Val Asp Lys Val Asn Glu Asn
                485                 490                 495

tgg aaa cgc tac ggc tat aaa taa                                      1512
Trp Lys Arg Tyr Gly Tyr Lys
            500


<210> SEQ ID NO 4
<211> LENGTH: 503
<212> TYPE: PRT
<213> ORGANISM: Artificial Sequence
<220> FEATURE:
<223> OTHER INFORMATION: Synthetic Construct

<400> SEQUENCE: 4

Met Arg Lys Leu Asn Pro Ala Leu Glu Phe Arg Asp Phe Ile Gln Val
1               5                   10                  15

Leu Lys Asp Glu Asp Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
            180                 185                 190

His Ile Arg Gln Ile Ala Asp Ser Trp Ala Ala Ile Gly Lys Ala Asn
        195                 200                 205

Glu Ile Pro Phe Ala Leu Cys Phe Gly Val Pro Pro Ala Ala Ile Leu
    210                 215                 220
```

```
Val Ser Ser Met Pro Ile Pro Glu Gly Val Ser Glu Ser Asp Tyr Val
225                 230                 235                 240

Gly Ala Ile Leu Gly Glu Ser Val Pro Val Val Lys Cys Glu Thr Asn
                245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
        275                 280                 285

Tyr Val Phe Lys Ser Gln Gly His Pro Cys Pro Leu Tyr Thr Val Lys
    290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500


<210> SEQ ID NO 5
<211> LENGTH: 500
<212> TYPE: PRT
<213> ORGANISM: Aspergillus niger

<400> SEQUENCE: 5

Met Ser Ala Gln Pro Ala His Leu Cys Phe Arg Ser Phe Val Glu Ala
1               5                   10                  15

Leu Lys Val Asp Asn Asp Leu Val Glu Ile Asn Thr Pro Ile Asp Pro
            20                  25                  30

Asn Leu Glu Ala Ala Ala Ile Thr Arg Arg Val Cys Glu Thr Asn Asp
        35                  40                  45

Lys Ala Pro Leu Phe Asn Asn Leu Ile Gly Met Lys Asn Gly Leu Phe
    50                  55                  60

Arg Ile Leu Gly Ala Pro Gly Ser Leu Arg Lys Ser Ser Ala Asp Arg
65                  70                  75                  80

Tyr Gly Arg Leu Ala Arg His Leu Ala Leu Pro Pro Thr Ala Ser Met
                85                  90                  95
```

-continued

```
Arg Glu Ile Leu Asp Lys Met Leu Ser Ala Ser Asp Met Pro Pro Ile
            100                 105                 110

Pro Pro Thr Ile Val Pro Thr Gly Pro Cys Lys Glu Asn Ser Leu Asp
        115                 120                 125

Asp Ser Glu Phe Asp Leu Thr Glu Leu Pro Val Pro Leu Ile His Lys
    130                 135                 140

Ser Asp Gly Gly Lys Tyr Ile Gln Thr Tyr Gly Met His Ile Val Gln
145                 150                 155                 160

Ser Pro Asp Gly Thr Trp Thr Asn Trp Ser Ile Ala Arg Ala Met Val
                165                 170                 175

His Asp Lys Asn His Leu Thr Gly Leu Val Ile Pro Pro Gln His Ile
            180                 185                 190

Trp Gln Ile His Gln Met Trp Lys Lys Glu Gly Arg Ser Asp Val Pro
        195                 200                 205

Trp Ala Leu Ala Phe Gly Val Pro Pro Ala Ala Ile Met Ala Ser Ser
    210                 215                 220

Met Pro Ile Pro Asp Gly Val Thr Glu Ala Gly Tyr Val Gly Ala Met
225                 230                 235                 240

Thr Gly Ser Ser Leu Glu Leu Val Lys Cys Asp Thr Asn Asp Leu Tyr
                245                 250                 255

Val Pro Ala Thr Ser Glu Ile Val Leu Glu Gly Thr Leu Ser Ile Ser
            260                 265                 270

Glu Thr Gly Pro Glu Gly Pro Phe Gly Glu Met His Gly Tyr Ile Phe
        275                 280                 285

Pro Gly Asp Thr His Leu Gly Ala Lys Tyr Lys Val Asn Arg Ile Thr
    290                 295                 300

Tyr Arg Asn Asn Ala Ile Met Pro Met Ser Ser Cys Gly Arg Leu Thr
305                 310                 315                 320

Asp Glu Thr His Thr Met Ile Gly Ser Leu Ala Ala Ala Glu Ile Arg
                325                 330                 335

Lys Leu Cys Gln Gln Asn Asp Leu Pro Ile Thr Asp Ala Phe Ala Pro
            340                 345                 350

Phe Glu Ser Gln Val Thr Trp Val Ala Leu Arg Val Asp Thr Glu Lys
        355                 360                 365

Leu Arg Ala Met Lys Thr Thr Ser Glu Gly Phe Arg Lys Arg Val Gly
    370                 375                 380

Asp Val Val Phe Asn His Lys Ala Gly Tyr Thr Ile His Arg Leu Val
385                 390                 395                 400

Leu Val Gly Asp Asp Ile Asp Val Tyr Glu Gly Lys Asp Val Leu Trp
                405                 410                 415

Ala Phe Ser Thr Arg Cys Arg Pro Gly Met Asp Glu Thr Leu Phe Glu
            420                 425                 430

Asp Val Arg Gly Phe Pro Leu Ile Pro Tyr Met Gly His Gly Asn Gly
        435                 440                 445

Pro Ala His Arg Gly Gly Lys Val Val Ser Asp Ala Leu Met Pro Thr
    450                 455                 460

Glu Tyr Thr Thr Gly Arg Asn Trp Glu Ala Ala Asp Phe Asn Gln Ser
465                 470                 475                 480

Tyr Pro Glu Asp Leu Lys Gln Lys Val Leu Asp Asn Trp Thr Lys Met
                485                 490                 495

Gly Phe Ser Asn
            500
```

<210> SEQ ID NO 6
<211> LENGTH: 570
<212> TYPE: DNA
<213> ORGANISM: Escherichia coli
<220> FEATURE:
<221> NAME/KEY: CDS
<222> LOCATION: (1)..(570)
<223> OTHER INFORMATION: Flavin prenyltransferase

<400> SEQUENCE: 6

```
atg aaa cga ctc att gta ggc atc agc ggt gcc agc ggc gcg att tat       48
Met Lys Arg Leu Ile Val Gly Ile Ser Gly Ala Ser Gly Ala Ile Tyr
1               5                   10                  15

ggc gtg cgc tta tta cag gtt ctg cgc gat gtc aca gat atc gaa acg       96
Gly Val Arg Leu Leu Gln Val Leu Arg Asp Val Thr Asp Ile Glu Thr
            20                  25                  30

cat ctg gtg atg agc cag gca gcg cgc cag acc tta tcc ctc gaa acg      144
His Leu Val Met Ser Gln Ala Ala Arg Gln Thr Leu Ser Leu Glu Thr
        35                  40                  45

gat ttt tct ctg cgc gaa gtg cag gca tta gcc gat gtc acg cac gat      192
Asp Phe Ser Leu Arg Glu Val Gln Ala Leu Ala Asp Val Thr His Asp
    50                  55                  60

gcg cgc gat att gcc gcc agc atc tct tcc ggt tct ttc cag acg ctg      240
Ala Arg Asp Ile Ala Ala Ser Ile Ser Ser Gly Ser Phe Gln Thr Leu
65                  70                  75                  80

ggg atg gtg att tta ccc tgt tca atc aaa acc ctt tcc ggc att gtc      288
Gly Met Val Ile Leu Pro Cys Ser Ile Lys Thr Leu Ser Gly Ile Val
                85                  90                  95

cat agc tat act gat ggc tta ctg acc cgt gcg gca gat gtg gtg ctg      336
His Ser Tyr Thr Asp Gly Leu Leu Thr Arg Ala Ala Asp Val Val Leu
            100                 105                 110

aaa gag cgt cgc ccg ttg gtg ctc tgc gtg cgt gaa aca cca ttg cac      384
Lys Glu Arg Arg Pro Leu Val Leu Cys Val Arg Glu Thr Pro Leu His
        115                 120                 125

tta ggc cat ctg cgt tta atg act cag gcg gca gaa atc ggt gcg gtg      432
Leu Gly His Leu Arg Leu Met Thr Gln Ala Ala Glu Ile Gly Ala Val
    130                 135                 140

att atg cct ccc gtt ccg gcg ttt tat cat cgc ccg caa tcc ctt gat      480
Ile Met Pro Pro Val Pro Ala Phe Tyr His Arg Pro Gln Ser Leu Asp
145                 150                 155                 160

gat gtg ata aat cag acg gtt aat cgt gtt ctt gac cag ttt gcg ata      528
Asp Val Ile Asn Gln Thr Val Asn Arg Val Leu Asp Gln Phe Ala Ile
                165                 170                 175

acc ctt cct gaa gat ctc ttt gcc cgc tgg cag ggc gca taa              570
Thr Leu Pro Glu Asp Leu Phe Ala Arg Trp Gln Gly Ala
            180                 185
```

<210> SEQ ID NO 7
<211> LENGTH: 189
<212> TYPE: PRT
<213> ORGANISM: Escherichia coli

<400> SEQUENCE: 7

```
Met Lys Arg Leu Ile Val Gly Ile Ser Gly Ala Ser Gly Ala Ile Tyr
1               5                   10                  15

Gly Val Arg Leu Leu Gln Val Leu Arg Asp Val Thr Asp Ile Glu Thr
            20                  25                  30

His Leu Val Met Ser Gln Ala Ala Arg Gln Thr Leu Ser Leu Glu Thr
        35                  40                  45

Asp Phe Ser Leu Arg Glu Val Gln Ala Leu Ala Asp Val Thr His Asp
    50                  55                  60
```

-continued

```
Ala Arg Asp Ile Ala Ala Ser Ile Ser Ser Gly Ser Phe Gln Thr Leu
65                  70                  75                  80

Gly Met Val Ile Leu Pro Cys Ser Ile Lys Thr Leu Ser Gly Ile Val
                85                  90                  95

His Ser Tyr Thr Asp Gly Leu Leu Thr Arg Ala Ala Asp Val Val Leu
            100                 105                 110

Lys Glu Arg Arg Pro Leu Val Leu Cys Val Arg Glu Thr Pro Leu His
        115                 120                 125

Leu Gly His Leu Arg Leu Met Thr Gln Ala Ala Glu Ile Gly Ala Val
    130                 135                 140

Ile Met Pro Pro Val Pro Ala Phe Tyr His Arg Pro Gln Ser Leu Asp
145                 150                 155                 160

Asp Val Ile Asn Gln Thr Val Asn Arg Val Leu Asp Gln Phe Ala Ile
                165                 170                 175

Thr Leu Pro Glu Asp Leu Phe Ala Arg Trp Gln Gly Ala
            180                 185
```

METHOD OF PRODUCING UNSATURATED HYDROCARBON COMPOUNDS WITH MUTATED FERULIC ACID FROM *SACCHAROMYCES*

TECHNICAL FIELD

The present invention relates to a decarboxylase in which the amino acid at position 398 is substituted with another amino acid such as glutamine in a ferulic acid decarboxylase derived from bacteria belonging to the genus *Saccharomyces*, a DNA encoding the decarboxylase, a vector inserted with the DNA, and a host cell introduced with the DNA or the vector. The present invention also relates to a method for producing an unsaturated hydrocarbon compound using the decarboxylase or the host cell. The present invention also relates to an agent for promoting the production of an unsaturated hydrocarbon compound, including the decarboxylase, the DNA, or the vector. The present invention also relates to a method for producing the decarboxylase.

BACKGROUND

It can be said that butadiene (1,3-butadiene) is an extremely important organic compound in the chemical industry because it is used as a raw material for various polymer compounds such as various synthetic rubbers (such as butadiene rubber, styrene-butadiene rubber, and acrylonitrile-butadiene rubber) and polymer resins (such as ABS resin and nylon 66). Further, these polymer compounds made from butadiene are widely used not only in industrial products such as automobile tires but also in daily necessities such as clothing. As a result, the demand for butadiene is increasing year by year, with annual demand reaching 13 million tons and a market size of $15 billion.

Traditionally, butadiene has been produced mainly by purifying the C4 fraction produced as a by-product in the production of ethylene and propylene from petroleum. However, due to environmental problems such as the depletion of fossil fuels including petroleum and global warming due to greenhouse gas emissions, there is an increasing need to achieve sustainable butadiene production in order to meet the ever-increasing demand for butadiene mentioned above. Thus, as a countermeasure, a method for producing butadiene from a substance derived from a biomass resource, which is a renewable resource, using an enzyme is being actively developed.

For example, PTL 1 discloses a method for producing butadiene using xylose as a raw material and a microorganism having an enzymatic activity capable of converting it into crotyl alcohol or the like. Further, PTL 2 discloses a method for producing butadiene using xylose as a raw material and a microorganism having an enzymatic activity capable of converting it into 2,3-butanediol. As described above, many attempts have been made to produce unsaturated hydrocarbon compounds such as butadiene using enzymes.

Furthermore, the present inventors have made it clear that the production of 4-vinylguaiyacol (4VG) by the decarboxylation reaction of ferulic acid, which involves ferulic acid decarboxylase (FDC) (see NPL 1 and the following formula), can be applied to the production of unsaturated hydrocarbon compounds such as butadiene (PTL 3)

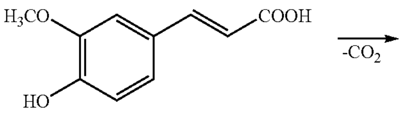

-continued

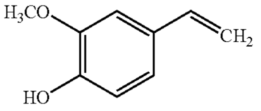

Specifically, it has been round by the present inventors that by introducing a mutation into the amino acid of FDC and changing the substrate specificity of the enzyme from the original ferulic acid to that for muconic acid or the like, butadiene and the like can be produced through a decarboxylation reaction as shown in the following formula.

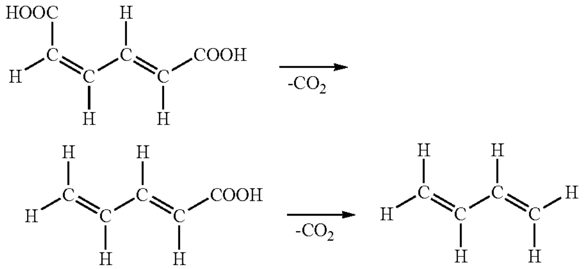

More specifically, the present inventors previously introduced mutations with amino acid substitutions into various positions of FDC derived from *Aspergillus* (decarboxylase composed of the amino acid sequence set forth in SEQ ID NO: 5) to prepare mutants. Then, these mutants were evaluated in terms of the catalytic activity for the production of butadiene using muconic acid as a substrate. As a result, it has been clarified that in FDC derived from *Aspergillus*, substitution of threonine at position 395 with another amino acid (glutamine, histidine, asparagine, lysine, serine, or arginine) generally improves the catalytic activity for the production of butadiene (improves the catalytic activity at least about 3 times as compared with the wild-type FDC before the mutation introduction). Furthermore, it has been clarified that in addition to the amino acid substitution at position 395, substitution of tyrosine at position 394 with another amino acid (phenylalanine, methionine, tryptophan, leucine, isoleucine, histidine, threonine, arginine, or asparagine) can further improve the catalytic activity for the production of 1,3-butadiene (PTL 3).

CITATION LIST

Patent Literature

[PTL 1] Japanese Patent Application Publication No. 2014-30376

[PTL 2] Japanese Patent Application Publication No. 2015-228804

[PTL 3] International Publication No. 2019-022083

Non Patent Literature

[NPL 1] Karl A. P. Payne et al., Nature, published on Jun. 25, 2015, Vol. 522, Issue 7557, pp. 497 to 501

SUMMARY

Technical Problem

An object of the present invention is to provide an enzyme capable of producing an unsaturated hydrocarbon compound such as butadiene with high productivity.

Solution to Problem

In order to achieve the above object, the present inventors evaluated the catalytic activity of ferulic acid decarboxylases (FDCs) derived from various microorganisms for the formation of unsaturated hydrocarbon compounds thereof. As a result, it has been found that the aforementioned catalytic activity of the wild-type FDC derived from *Saccharomyces cerevisiae* (decarboxylase composed of the amino ac id sequence set forth in SEQ ID NO: 2) was orders of magnitude higher (about 20 times) than that of the wild-type FDC derived from *Aspergillus* disclosed in PTT 3.

Further, it has been clarified that substitution of isoleucine at position 398 of the *Saccharomyces cerevisiae*-derived FDC with another amino acid (glutamine, methionine, asparagine, phenylalanine, histidine, or threonine) generally improves the catalytic activity for the production of butadiene (improves the catalytic activity at least about 3 times as compared with the wild-type FDC before the mutation introduction). In particular, it was found that the FDC mutant in which the aforementioned position was substituted with glutamine and the FDC mutant in which the aforementioned position was substituted with methionine had their catalytic activities improved 9.3 times and 16.4 times, respectively, as compared with the *Saccharomyces cerevisiae*-derived wild-type FDC.

Furthermore, in these *Saccharomyces*-derived FDCs in which phenylalanine at position 398 was substituted with another amino acid, mutants in which phenylalanine at position 397 was further substituted with another amino acid were also prepared, and the catalytic activity was evaluated for them as well. As a result, it was clarified that substitution of position 397 with another amino acid in addition to the amino acid substitution at position 398 could further improve the catalytic activity. In particular, in the mutant in which position 398 was substituted with glutamine, when position 397 was substituted with histidine or methionine, the catalytic activity was improved 75.1 times and 33.8 times, respectively, as compared with the *Saccharomyces cerevisiae*-derived wild-type FDC. It was also found that in the mutant in which position 398 was substituted with methionine, when position 397 was substituted with histidine, the catalytic activity was improved 37.3 times as compared with the *Saccharomyces cerevisiae*-derived wild-type FDC.

Further, it has also been found that in the above-mentioned mutants in which the amino acids at positions 398 and 397 are substituted with other amino acids, substitution of the amino acid at position 286, 334, 440, 189, or 326 with other amino acid further improves the catalytic activity. Thus, the present invention has been completed.

Specifically, the present invention relates to a decarboxylase in which the amino acid at position 398 in FDC derived from *Saccharomyces* is substituted with another amino acid such as glutamine, and a method for producing the same, and further relates to a DNA encoding the decarboxylase, a vector inserted with the DNA, a host cell introduced with the DNA or the vector. The present invention also relates to a method for producing an unsaturated hydrocarbon compound using the decarboxylase or the host cell. The present invention further relates to an agent for promoting the production of an unsaturated hydrocarbon compound, including the decarboxylase, the DNA, or the vector.

More specifically, the present invention provides the following.

<1>

A feruilic acid decarboxylase derived from *Saccharomyces* in which an amino acid at position 398 of an amino acid sequence set forth in SEQ ID NO: 2 or corresponding to the position is substituted with glutamine, methionine, asparagine, phenylalanine, histidine, or threonine, and which has a catalytic activity for producing an unsaturated hydrocarbon compound represented by the following formula (2) or (5) or a geometric isomer thereof (2)

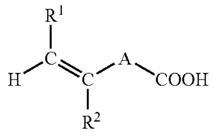

(5)

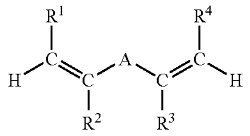

[in the formulas (2) and (5), "$R^1$," "$R^2$" "$R^3$," and "$R^4$" each independently represent a hydrogen atom, a linear or branched alkyl group having 1 to 5 carbon atoms, a linear or branched alkoxy group having 1 to 5 carbon atoms, or a hydroxyl group. "A" represents an optionally substituted linear hydrocarbon group having 0 to 5 carbon atoms, and when the number of carbon atoms is 2 to 5, a double bond may be formed between adjacent carbon atoms].

<2>

The ferulic acid decarboxylase according to <1>, wherein the amino acid at position 397 of the amino acid sequence set forth in SEQ ID NO: 2 or corresponding to the position is substituted with histidine or methionine.

<3>

A DNA encoding the ferulic acid decarboxylase according to <1> or <2>.

<4>

A vector comprising: the DNA according to <3>.

<5>

A host: cell introduced with the DNA according to <3> or the vector according to <4>.

<6>

A method for producing an unsaturated hydrocarbon compound represented by the following formula (2) or a geometric isomer thereof, comprising the steps of: decarboxylating an unsaturated hydrocarbon dicarboxylic ac id compound represented by the following formula (1) or a geometric isomer thereof in the presence of the ferulic acid decarboxylase according to <1> or <2>

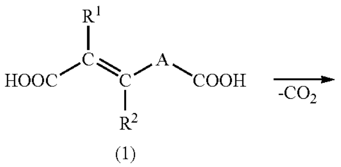

(1)

-continued

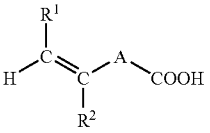

(2)

[in the formula (1) and (2), "$R^1$" and "$R^2$" each independently represent a hydrogen atom, a linear or branched alkyl group having 1 to 5 carbon atoms, a linear or branched alkoxy group having 1 to 5 carbon atoms, or a hydroxyl group. "A" represents an optionally substituted linear hydrocarbon group having 0 to 5 carbon atoms, and when the number of carbon atoms is 2 to 5, a double bond may be formed between adjacent carbon atoms].

<7>

A method for producing an unsaturated hydrocarbon compound represented by the following formula (5) or a geometric isomer thereof, comprising the steps of: decarboxylating an unsaturated hydrocarbon dicarboxylic acid compound represented by the following formula (3) or a geometric isomer thereof in the presence of the ferulic acid decarboxylase according to <1> or <2>

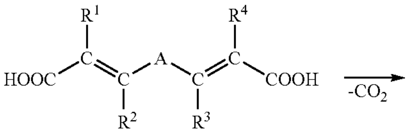

(3)

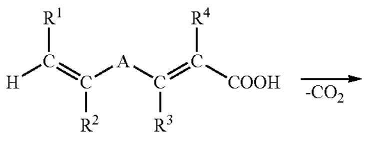

(4)

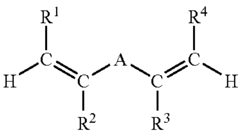

(5)

[in the formula (3) to (5), "$R^1$," "$R^2$," "$R^3$" and "$R^4$" each independently represent a hydrogen atom, a linear or branched alkyl group having 1 to 5 carbon atoms, a linear or branched alkoxy group having 1 to 5 carbon atoms, or a hydroxyl group. "A" represents an optionally substituted linear hydrocarbon group having 0 to 5 carbon atoms, and when the number of carbon atoms is 2 to 5, a double bond may be formed between adjacent carbon atoms].

<8>

A method for producing an unsaturated hydrocarbon compound, comprising the steps of: culturing the host cell according to <5>; and collecting an unsaturated hydrocarbon compound represented by the following formula (2) or (5) or a geometric isomer thereof produced in the host cell and/or a culture product thereof (2)

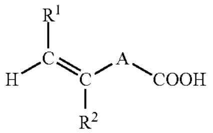

(5)

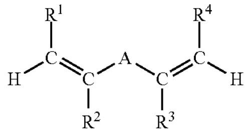

[in the formulas (2) and (5), "$R^1$," "$R^2$," "$R^3$," and "$R^4$" each independently represent a hydrogen atom, a linear or branched alkyl group having 1 to 5 carbon atoms, a linear or branched alkoxy group having 1 to 5 carbon atoms, or a hydroxyl group. "A" represents an optionally substituted linear hydrocarbon group having 0 to 5 carbon atoms, and when the number of carbon atoms is 2 to 5, a double bond may be formed between adjacent carbon atoms].

<9>

An agent for decarboxylating an unsaturated hydrocarbon dicarboxylic acid compound represented by the following formula (1) or a geometric isomer thereof and promoting production of an unsaturated hydrocarbon compound represented by the following formula (2) or a geometric isomer thereof, comprising: the ferulic acid decarboxylase according to < >1 or <2>, the DNA according to <3>, or the vector according to <4>

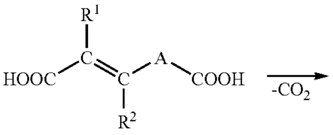

(1)

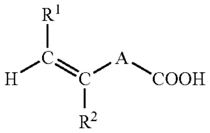

(2)

[in the formula (1) and (2), "$R^1$" and "$R^2$" each independently represent a hydrogen atom, a linear or branched alkyl group having 1 to 5 carbon atoms, a linear or branched alkoxy group having 1 to 5 carbon atoms, or a hydroxyl group. "A" represents an optionally substituted linear hydrocarbon group having 0 to 5 carbon atoms, and when the number of carbon atoms is 2 to 5, a double bond may be formed between adjacent carbon atoms].

<10>

An agent for decarboxylating an unsaturated hydrocarbon dicarboxylic acid compound represented by the following formula (3) or a geometric isomer thereof and promoting production of an unsaturated hydrocarbon compound represented by the following formula (5) or a geometric isomer thereof, comprising: the ferulic acid decarboxylase according to <1> or <2>, the DNA according to <3>, or the vector according to <4>

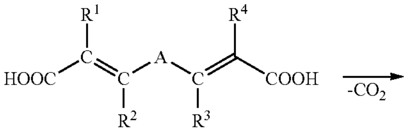

(3)

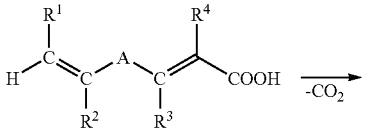

(4)

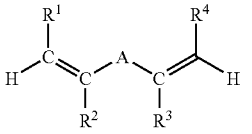

(5)

[in the formula (3) to (5), "$R^1$," "$R^2$" "$R^3$," and "$R^4$" each independently represent a hydrogen atom, a linear or branched alkyl group having 1 to 5 carbon atoms, a linear or branched alkoxy group having 1 to 5 carbon atoms, or a hydroxyl group. "A" represents an optionally substituted linear hydrocarbon group having 0 to 5 carbon atoms, and when the number of carbon atoms is 2 to 5, a double bond may be formed between adjacent carbon atoms].

<11>

The agent according to <9> or <10>, wherein the ferulic acid decarboxylase is a ferulic acid decarboxylase in which an amino acid at position 398 of an amino acid sequence set forth in SEQ ID NO: 2 or corresponding to the posit ion is glutamine or methionine, and an amino acid at position 397 of the amino acid sequence set forth in SEQ ID NO: 2 or corresponding to the position is histidine or methionine.

<12>

A method for producing a mutant of ferulic acid decarboxylase derived from *Saccharomyces*, comprising the steps of: culturing the host cell according to <5>; and collecting a protein expressed in the host cell.

<13>

A method for producing a ferulic acid decarboxylase having enhanced catalytic activity for producing an unsaturated hydrocarbon compound represented by the following formula (2) or (5) or a geometric isomer thereof, comprising the steps of: substituting, in a ferulic acid decarboxylase derived from *Saccharomyces*, an amino acid at position 398 of an amino acid sequence set forth in SEQ ID NO: 2 or corresponding to the position with glutamine, methionine, asparagine, phenylalanine, histidine, or threonine (2)

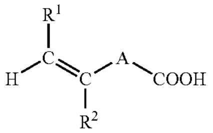

(5)

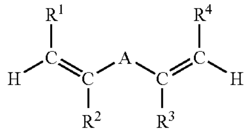

[in the formulas (2) and (5), "$R^1$," "$R^2$," "$R^3$," and "$R^4$" each independently represent a hydrogen atom, a linear or branched alkyl group having 1 to 5 carbon atoms, a linear or branched alkoxy group having 1 to 5 carbon atoms, or a hydroxyl group. "A" represents an optionally substituted linear hydrocarbon group having 0 to 5 carbon atoms, and when the number of carbon atoms is 2 to 5, a double bond may be formed between adjacent carbon atoms].

<14>

The production method according to <13>, further comprising: substituting, in the ferulic acid decarboxylase, an amino acid at position 397 of an amino acid sequence set forth in SEQ ID NO: 2 or corresponding to the position with histidine or methionine.

Advantageous Effects of Invention

The present invention makes it possible to provide an enzyme capable of producing an unsaturated hydrocarbon compound such as butadiene with high productivity, and a method for producing an unsaturated hydrocarbon compound using the enzyme.

DETAILED DESCRIPTION

<Ferulic Acid Decarboxylase Mutant>

As shown in Examples described later, it has been clarified that the ferulic acid decarboxylase (FDC) derived from *Saccharomyces* has about 20 times higher catalytic activity of promoting the following reactions to produce an unsaturated hydrocarbon compound represented by the following formula (2) or (5), or a geometric isomer thereof (also referred to as "catalytic activity for producing unsaturated hydrocarbon compounds") than that derived from *Aspergillus* disclosed in PTL 3.

Further, it has been clarified that in FDC derived from *Saccharomyces cerevisiae* (decarboxylase composed of the amino acid sequence set forth in SEQ ID NO: 2), substitution of the amino acid at position 398 with another amino acid (glutamine, methionine, asparagine, phenylalanine, histidine, or threonine) further improves the catalytic activity.

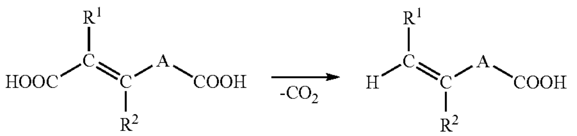

(1) (2)

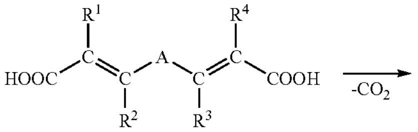

(3)

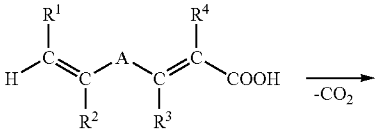

(4)

-continued

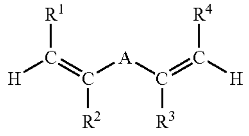

(5)

Therefore, the present invention provides a ferulic acid decarboxylase derived from *Saccharomyces* in which an amino acid at position 398 of an amino acid sequence set forth in SEQ ID NO: 2 or corresponding to the position is substituted with glutamine, methionine, asparagine, phenylalanine, histidine, or threonine, and which has a catalytic activity for producing an unsaturated hydrocarbon compound represented by the formula (2) or (5) or a geometric isomer thereof (hereinafter also referred to as an FDC mutant of the present invention).

The "ferulic acid decarboxylase (FDC)" is usually an enzyme registered as EC number: 4.1.1.102, and means an enzyme that catalyzes the following reaction for decarboxylating ferulic acid to produce 4-vinylguaiyacol (4VG).

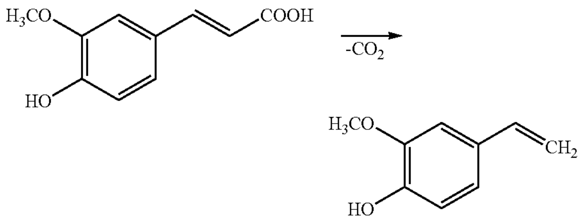

In the FDC mutant of the present invention, the FDC subjected to amino acid substitution may be one derived from *Saccharomyces*. In the present invention, "*Saccharomyces*" means a bacterium belonging to the genus *Saccharomyces*, and examples thereof include *Saccharomyces cerevisiae, Saccharomyces kudriavzevii, Saccharomyces eubayanus, Saccharomyces bayanus, Saccharomyces boulardii, Saccharomyces bulderi, Saccharomyces cariocanus, Sacchiaromyces cariocus, Saccharomyces chevalieri, Saccharomyces dairenensis, Saccharomyces ellipsoideus, Saccharomyces florentinus, Saccharomyces kiuyveri, Saccharomyces martiniae, Saccharomyces monacensis, Saccharomyces norbensis, Saccharomyces paradoxus, Saccharomyces pastorianus, Saccharomyces spenceorum, Saccharomyces turicensis, Saccharomyces unisporus, Saccharomyces uvarum*, and *Saccharomyces zonatus*.

Examples of the FDC derived from *Saccharomyces* include an FDC derived from *Saccharomyces cerevisiae* (ATCC 204508/S288c strain) (baker's yeast) (UNIPROT ID: Q03034, FDC composed of the amino acid sequence set forth in SEQ ID NO: 2), as well as a protein derived from *Saccharomyces* corresponding to "Ferulic acid decarboxylase" on UNIPROT, and more specifically include the FDCs presented in Table 1 below. Note that it should be understood mutations in a nucleotide sequence in nature can result in changes in the amino acid sequence of the protein.

TABLE 1

| Uniprot_ID | Entry Name | Origin | (Number of Amino Acid Residues Matching Sequence Set Forth in SEQ ID NO: 2)/(Number of Amino Acid Residues Set Forth in SEQ ID NO: 2) [%] | (Number of Amino Acid Residues Matching Sequence Set Forth in SEQ ID NO: 2)/(Number of Amino Acid Residues of FDC Derived from X) [%] |
|---|---|---|---|---|
| Q03034 | FDC1_YEAST | *Saccharomyces cerevisiae* (strain ATCC 204508/S288c) (Baker's yeast) | 100.0 | 100.0 |
| H0GEV9 | H0GEV9_SACCK | *Saccharomyces cerevisiae* × *Saccharomyces kudriavzevii* (strain VIN7) | 99.8 | 99.8 |
| E9P8F2 | E9P8F2_YEASX | *Saccharomyces cerevisiae* | 99.8 | 99.8 |
| E9P8F1 | E9P8F1_YEASX | *Saccharomyces cerevisiae* | 99.8 | 99.8 |
| A6ZZC4 | A6ZZC4_YEAS7 | *Saccharomyces cerevisiae* (strain YJM789) | 99.8 | 99.8 |
| N1P7L1 | N1P7L1_YEASC | *Saccharomyces cerevisiae* strain CEN.PK113-7D | 98.6 | 100 |
| H0GTK3 | H0GTK3_SACCK | *Saccharomyces cerevisiae* × *Saccharomyces kudriavzevii* (strain VIN7) | 89.1 | 89.1 |
| J8TRN5 | J8TRN5_SACK1 | *Saccharomyces kudriavzevii* (strain ATCC MYA-4449/AS 2.2408/CBS 8840/NBRC 1802/NCYC 2889) | 88.9 | 88.9 |
| A0A0L8RE03 | A0A0L8RE03_SACEU | *Saccharomyces eubayanus* | 88.3 | 88.3 |

Among the FDCs presented in Table 1, as the FDC subjected to amino acid substitution, the FDC derived from *Saccharomyces cerevisiae* is preferable, and the protein composed of the amino acid sequence set forth in SEQ ID NO: 2 is more preferable.

Further, in the present invention, the FDC derived from *Saccharomyces* introduced a mutation accompanied by an amino acid substitution has an identity of preferably 80% or more (for example, 81% or more, 82% or more, 83% or more, and 84% or more), more preferably 85% or more (for example, 86% or more, 87% or more, 88% or more, and 89% or more), further preferably 90% or more (for example, 91% or more, 92% or more, 93% or more, and 94% or more), and more preferably 95% or more (for example, 96% or more, 97% or more, 98% or more, and 99% or more) with the amino acid sequence set forth in SEQ ID NO: 2. Note that in the present invention, "identity" means the ratio (%) of the number of amino acids matching the FDC and the amino acid sequence set forth in SEQ ID NO: 2 to the total number of amino acids of the *Saccharomyces*-derived FDC.

In the present invention, the mutation accompanied by the amino acid substitution introduced into the FDC derived from *Saccharomyces* described above is not limited to an artificial one as shownin Examples described later, and may be a naturally occurring mutation. Further, as shown in Examples described later, the mutation introduced at position 398 of the amino acid sequence set forth in SEQ ID NO: 2 or the position corresponding thereto may be accompanied by substitution with glutamine, methionine, asparagine, phenylalanine, histidine, or threonine, but from the viewpoint of higher catalytic activity for producing unsaturated hydrocarbon compounds, it is preferably a substitution with glutamine or methionine, and particularly preferably a substitution with glutamine.

The FDC mutant of the present invention may be one in which a mutation is introduced to other than the aforementioned amino acid at position 398 of the amino acid sequence set forth in SEQ ID NO: 2 or corresponding to the position. Specifically, the FDC mutant of the present invention also includes a protein composed of an amino acid sequence in which one or more amino acids are substituted, deleted, added, and/or inserted at positions other than position 398 of the amino acid sequence (such as the amino acid sequence set forth in SEQ ID NO: 2) of the *Saccharomyces*-derived FDC. Here, the term "more" is not particularly limited, but is usually 2 to 100, preferably 2 to 50, more preferably 2 to 40, further preferably 2 to 30, more preferably 2 to 20, and further preferably 2 to 10 (for example, 2 to 8, 2 to 4, and 2).

Such mutations are not particularly limited as long as the FDC mutant of the present invention has a catalytic activity for producing unsaturated hydrocarbon compounds, and examples thereof include mutations accompanied by the following amino acid substitutions.

As shown in Examples described later, in the FDC mutant of the present invention, the catalytic activity for producing unsaturated hydrocarbon compounds tends to be further increased, so that in addition to the amino acid substitution at position 398 described above, the amino acid at position 397 of the amino acid sequence set forth in SEQ ID NO: 2 or corresponding to the position is substituted with preferably histidine, methionine, tyrosine, or leucine, more preferably with histidine or methionine, and particularly preferably with histidine.

Further, as shown in Examples described later, in the FDC mutant of the present invention, the catalytic activity for producing unsaturated hydrocarbon compounds tends to be further increased, so that in addition to the amino acid substitutions at position 398 and position 397 described above, further, it is preferable that the amino acid at position 334 of the amino acid sequence set forth in SEQ ID NO: 2 or corresponding to the position is substituted with isoleucine, the amino acid at position 286 of the amino acid sequence set forth in SEQ ID NO: 2 or corresponding to the position is substituted with leucine, the amino acid at position 440 of the amino acid sequence set forth in SEQ ID NO: 2 or corresponding to the position is substituted with threonine, the amino acid at position 189 of the amino acid sequence set forth in SEQ ID NO: 2 or corresponding to the position is substituted with methionine, or the amino acid at position 326 of the amino acid sequence set forth in SEQ ID NO: 2 or corresponding to the position is substituted with leucine, and it is more preferable that the amino acid at position 334 of the amino acid sequence set forth in SEQ ID NO: 2 or corresponding to the position is substituted with isoleucine or the amino acid at position 286 of the amino acid sequence set forth in SEQ ID NO: 2 or corresponding to the position is substituted with leucine.

More specifically, the FDC mutant of the present invention is preferably a *Saccharomyces*-derived FDC mutant in which the amino acid at position 398 of the amino acid sequence set forth in SEQ ID NO: 2 or corresponding to the position is substituted with glutamine, and the amino acid at position 397 of the same amino acid sequence or corresponding the position is substituted with histidine, a *Saccharomyces*-derived FDC mutant in which the amino acid at position 398 of the amino acid sequence set forth in SEQ ID NO: 2 or corresponding to the position is substituted with glutamine, and the amino acid at position 397 of the same amino acid sequence or corresponding the position is substituted with methionine, or a *Saccharomyces*-derived FDC mutant in which the amino acid at position 398 of the amino acid sequence set forth in SEQ ID NO: 2 or corresponding to the position is substituted with methionine, and the amino acid at position 397 of the same amino acid sequence or corresponding the position is substituted with histidine.

Further, it is more preferably a *Saccharomyces*-derived FDC mutant in which the amino acid at position 398 of the amino acid sequence set forth in SEQ TD NO: 2 or corresponding to the position is substituted with glutamine, the amino acid at position 397 of the same amino acid sequence or corresponding the position is substituted with histidine, and the amino acid at position 286 of the same amino acid sequence or corresponding to the position is substituted with Leucine, or a *Saccharomyces*-derived FDC mutant in which the amino acid at position 398 of the amino acid sequence set forth in SEQ ID NO: 2 or corresponding to the position is substituted with glutamine, the amino acid at position 397 of the same amino acid sequence or corresponding the position is substituted with histidine, and the amino acid at position 334 of the same amino acid sequence or corresponding to the position is substituted with isoleucine.

Note that in the present invention, a "corresponding position" is a position in the same row as isoleucine or the like at position 398 in the amino acid sequence set forth in SEQ ID NO: 2 when the amino acid sequence set forth in SEQ ID NO: 2 and the amino acid sequence such as FDC derived from another bacterium belonging to the genus *Saccharomyces* are aligned using nucleotide and amino acid sequence analysis software (such as GENETYX-MAC or Sequencher) and BLAST (blast.ncbi.nlm.nih.gov/Blast.cgi).

Further, whether or not the FDC mutant of the present invention has a catalytic activity for producing unsaturated hydrocarbon compounds is determined by, for example, directly measuring the amount of the unsaturated hydrocarbon compound by gas chromatography-mass spectrometry (GC-MS), as shown in Examples described later. Furthermore, by comparing with the amount in the wild-type FDC derived from *Saccharomyces* such as FDC composed of the amino acid sequence set forth in SEQ ID NO: 2, it can also be determined whether or not the catalytic activity for producing unsaturated hydrocarbon compounds is higher than that of the wild-type FDC.

The FDC mutant of the present invention has a catalytic activity for producing unsaturated hydrocarbon compounds which is preferably twice or more (for example, 3 times or more, 4 times or more, 5 times or more, 6 times or more, 7 times or more, 8 times or more, and 9 times or more), more preferably 10 times or more (for example, 20 times or more, 30 times or more, and 40 times or more), further preferably 50 times or more (for example, 60 times or more, 70 times or more, 80 times or more, and 90 times or more), and more preferably 100 times or more that of the wild-type FDC derived from *Saccharomyces* (for example, the FDC composed of the amino acid sequence set forth in SEQ ID NO: 2).

Further, the FDC mutant of the present invention has a catalytic activity for producing unsaturated hydrocarbon compounds which is preferably 30 times or more (for example, 40 times or more, 50 times or more, 60 times or more, 70 times or more, 80 times or more, and 90 times or more), more preferably 100 times or more (for example, 200 times or more, 300 times or more, and 400 times or more), further preferably 500 times or more (for example, 600 times or more, 700 times or more, 800 times or more, and 900 times or more), further preferably 1000 times or more (for example, 1100 times or more, 1200 times or more, 1300 times or more, and 1400 times or more), more preferably 1500 times or more (for example, 1600 times or more, 1700 times or more, 1800 times or more, and 1900 times or more), and particularly preferably 2000 times or more that of the FDC composed of the amino acid sequence set forth in SEQ ID NO: 5 (wild-type FDC derived from *Aspergillus*).

As the FDC mutant of the present invention, it is possible to use only one kind of ferulic acid decarboxylase derived from *Saccharomyces* in which the amino acid at position 398 of the amino acid sequence set forth in SEQ ID NO: 2 or corresponding to the position is glutamine or the like, but two or more kinds of the FDC mutant of the present invention can also be used in combination. Further, as shown in PTL 3, from the viewpoint of more facilitating decarboxylation of the unsaturated hydrocarbon carboxylic acid compound, an FDC may be used in combination in which the amino acid at position 398 of the amino acid sequence set forth in SEQ ID NO: 2 or corresponding to the position is threonine. Examples of FDCs in which the amino acid at position 398 of the amino acid sequence set forth in SEQ ID NO: 2 or corresponding to the position is threonine are presented in Tables 2 to 6 below.

TABLE 2

| Unipot_ID | Origin |
|---|---|
| A2QHE5 | *Aspergillus niger* |
| A0A1L9U2T1 | *Aspergillus brasiliensis* CBS 101740 |
| G7XVA2 | *Aspergilius kawachii* |
| A0A1L9NIV5 | *Aspergillus tubingensis* CBS 134.48 |
| A0A124BYZ7 | *Aspergillus niger* |
| A0A146FW50 | *Aspergillus luchuensis* |
| A0A1Q5UJS2 | *Penicillium subrubescens* |
| A0A1L9R520 | *Aspergillus wentii* DT0 134E9 |
| A0A0A2J5F4 | *Penicillium expansum* |
| K9FG02 | *Penicillium digitatum* |
| A0A017SAW2 | *Aspergillus ruber* CBS 135680 |
| A0A0G4P429 | *Penicillium camemberti* |
| A0A161XU08 | *Penicillium chrysogenum* |
| A0A0M9WF89 | *Penicillium nordicum* |
| A0A1L9VVP0 | *Aspergillus glaucus* CBS 516.65 |
| A0A1E3B147 | *Aspergillus cristatus* |
| A0A135LJP5 | *Penicillium patulum* |
| A0A0F7U117 | *Penicillium brasilianum* |
| A0A0D9NTQ8 | *Metarhizium anisopliae* BRIP 53293 |
| A0A0B4GIB4 | *Metarhizium guizhouense* ARSEF 977 |
| A0A014P6U4 | *Metarhizium robertsii* |
| W6QKP7 | *Penicillium roqueforti* (strain FM164) |
| A0A1F5L787 | *Penicillium arizonense* |

TABLE 3

| Unipot_ID | Origin |
|---|---|
| A0A0K8LG51 | *Aspergillus udagawae* |
| A0A0F0IHE5 | *Aspergillus parasiticus* |
| A0A1L9WTP9 | *Aspergillus aculeatus* ATCC 16872 |
| A0A1F8AA53 | *Aspergillus bombycis* |
| Q2UP67 | *Aspergillus oryzae* |
| A1DCG7 | *Neosartorya fischeri* |
| A0A0S7DJV6 | *Aspergillus lentulus* |
| A0A0L1J9Y6 | *Aspergillus nomius* NRRL 13137 |
| A0A0F8UFA2 | *Aspergillus rambellii* |
| A0A0U5FRV8 | *Aspergillus calidoustus* |
| A0A1L9PYZ1 | *Aspergillus versicolor* CBS 583.65 |
| A0A1L9T8N0 | *Aspergillus sydowii* CBS 593.65 |
| A0A060T4A6 | *Blastobotrys adeninivorans* |
| R1EM06 | *Botryosphaeria parva* |
| K2RUE8 | *Macrophomina phaseolina* |
| W9YNA8 | *Capronia coronata* CBS 617.96 |
| A0A1L7WNI4 | *Phialocephala subalpina* |
| G9MXT8 | *Hypocrea virens* |
| A0A0D0U0M0 | *Cryptococcus gattii* VG Ram5 |
| A0A095C6V3 | *Cryptococcus gattii* serotype B |
| A0A0G0A274 | *Trichoderma harzianum* |
| M3DF95 | *Sphaerulina musiva* (strain S02202) |
| J9VVU7 | *Cryptococcus neoformans* var. *grubii* serotype A |

TABLE 4

| Unipot_ID | *Origin* |
|---|---|
| A0A100IUI5 | *Aspergillus niger* |
| A0A094IED9 | *Pseudogymnoascus* sp. VKM F-4520 (FW-2644) |
| A0A0W7V9B7 | *Trichoderma gamsii* |
| A0A1L9N5Q2 | *Aspergillus tubingensis* CBS 134.48 |
| H3H3G9 | *Phytophthora ramorum* |
| G9NLP8 | *Hypocrea stroviridis* |
| M7THT1 | *Botryotinia fuckeliana* (strain BcDW1) |
| G2XWX0 | *Botryotinia fuckeliana* |
| A0A1L9WL61 | *Aspergillus aculeatus* ATCC 16872 |
| A0A1L7SUP6 | *Fusarium mangiferae* |
| N1RYW4 | *Fusarium oxysporum* f. sp. *cubense* (strain race 4) |
| F9FQB3 | *Fusarium oxysporum* |
| A0A0G2EQF2 | *Phaeomoniella chlamydospora* |
| W9HNN8 | *Fusarium oxysporum* FOSC 3-a |
| X0BC97 | *Fusarium oxysporum* f. sp. *raphani* 54005 |
| W9WWR1 | *Cladophialophora psammophila* CBS 110553 |
| A0A0D2DPQ1 | *Phialophora americana* |
| S0E299 | *Gibberella fujikuroi* |
| A0A0J0BVX6 | *Gibberella fujikuroi* |
| N4TMS4 | *Fusarium oxysporum* f. sp. *cubense* |
| W9JNI1 | *Fusarium oxysporum* Fo47 |
| A0A01QFR6 | *Colletotrichum fioriniae* PJ7 |

TABLE 5

| Unipot_ID | Origin |
|---|---|
| A0A0D2YAR9 | *Fusarium oxysporum* f. sp. *lycopersici* |
| A0A0D2IKD5 | *Cladophialophora bantiana* CBS 173.52 |
| A0A0D2AQI6 | *Cladophialophora immunda* |
| X0AT48 | *Fusarium oxysporum* f. sp. *melanis* 26406 |
| A0A135TY05 | *Colletotrichum nymphaeae* SA-01 |
| L2G6I9 | *Colletotrichum gloeosporioides* |
| A0A1L7VCR5 | *Fusarium proliferatum* ET1 |
| W3XQA0 | *Postalotiopsis fici* W106-1 |
| A0A135URQ4 | *Colletotrichum salicis* |
| A0A1G4BD14 | *Colletotrichum orchidophilum* |
| A0A1C1X2A9 | *Diaporthe helianthi* |
| W7MPM7 | *Gibberella moniliformis* |
| T0K816 | *Colletotrichum gloeosporioides* |
| A0A135RR59 | *Colletotrichum simmondsii* |
| A0A194V2G5 | *Valsa mali* var. *pyri* |
| A0A194VPQ6 | *Valsa mali* |

TABLE 5-continued

| Unipot_ID | Origin |
|---|---|
| W9NGN5 | *Fusarium oxysporum* f. sp. *pisi* HDV247 |
| E6RA84 | *Cryptococcus gatti* serotype B (strain WM276/ ATCC MYA-4071) |
| A0A0B7K683 | *Bionectria ochroleuca* |
| A0A0D0YJD0 | *Cryptucuccus gattii* EJB2 |
| A0A166MIL4 | *Colletotrichum tofieldiae* |
| A0A1J7J343 | *Coniochacta ligniaria* NRRL 30616 |

TABLE 6

| Unipot_ID | Origin |
|---|---|
| A0A0N8H5Z4 | *Neonectria ditissima* |
| S3D5R7 | *Ophiostoma piceae* |
| W9JP63 | *Fusarium oxysporum* Fo47 |
| W9ZFW9 | *Fusarium oxysporum* f. sp. *melonis* 26406 |
| F0XL98 | *Grosmannia clavigera* |
| W9HU82 | *Fusarium oxysporum* F0SC 3-a |
| H1VUR4 | *Colletotrichum higginsianum* (strain IMI 349063) |
| A0A0F9Z7X1 | *Trichoderma harzianum* |
| A0A0D0VV15 | *Cryptococcus gattii* CA1280 |
| A0A0D0X028 | *Cryptococcus gattii* VGIV IND107 |
| E6R9Z1 | *Cryptococcus gattii* serotype B |
| F0XKQ3 | *Grosmannia clavigera* |
| A0A0F4ZK68 | *Thielaviopsis punctulata* |
| G4YRJ8 | *Phytophthora sojae* |
| C7ZIA7 | *Nectria haematococca* |
| A0A0FBU179 | *Aspergillus ochraceoroseus* |
| C7ZC09 | *Nectria haematococca* |
| T2BN40 | *Cryptococcus neoformans* var. *grubii* serotype A |
| A0A0G2FUZ8 | *Diplodia seriata* |
| C5E506 | *Zygosaccharomyces rouxii* |
| A0A0T1WD51 | *Mycobacterium* sp. Root135 |
| A0A0A0WBD5 | *Phomopsis* liquidambaris |
| N1RLH9 | *Fusarium oxysporum* f. sp. *cubense* |

The FDC mutant of the present invention may be directly or indirectly added with a different compound. The addition is not particularly limited, and may be an addition at the gene level or a chemical addition. Further, the position to be added is not particularly limited, and may be either the amino terminal (hereinafter also referred to as "N-terminal") or the carboxyl terminal (hereinafter also referred to as "C-terminal") of the FDC mutant of the present invention, or both of them. Addition at the gene level is achieved by using a DNA encoding the FDC mutant of the present invention added to a DNA encoding another protein with matching reading frames. The "other proteins" added in this manner are not particularly limited, and for the purpose of facilitating the purification of the FDC mutant of the present invention, tagged proteins for purification such as polyhistidine (His-) tag protein, FLAG-tag® protein (registered trademark, Sigma-Aldrich), and glutathione-S-transferase (GST) are preferably used, and further, for the purpose of facilitating the detection or the FDC mutant of the present invention, tagged protein for detection such as fluorescent proteins such as GFP and chemiluminescent proteins such as luciferase are preferably used. The chemical addition may be covalent or non-covalent. The "covalent bond" is not particularly limited, and examples thereof include an amide bond between an amino group and a carboxyl group, an alkylamine bond between an amino group and an alkyl halide group, a disulfide bond between thiols, and a thioether bond between a thiol group and a maleimide group or an alkyl halide group. Examples of the "non-covalent bond" include a biotin-avidin bond. Further, as the "different compound" chemically added in this manner, for the purpose of facilitating the detection of the FDC mutant of the present invention, fluorescent dyes such as Cy3 and rhodamines are preferably used, for example.

Moreover, the FDC mutant of the present invention may be used by mixing with a different component. The different component is not particularly limited, and examples thereof include sterile water, physiological saline, vegetable oils, surfactants, lipids, solubilizer, buffers, protease inhibitors, and preservatives.

<DNA Encoding FDC Mutant of the Present Invention and Vector Having the DNA>

The DNA and the like encoding the FDC mutant of the present invention will be described. By introducing such DNA, it becomes possible to transform the traits of a host cell, so that the FDC mutant of the present invention can be produced in the cell, and thus an unsaturated hydrocarbon compound can be produced.

The DNA of the present invention may be a DNA formed by introducing a mutation into a natural DNA, or may be a DNA composed of an artificially designed nucleotide sequence, as long as it encodes the FDC mutant of the present invention described above. Further, the morphology thereof is not particularly limited, and includes cDNA as well as genomic DNA and chemically synthesized DNA. Preparation of these DNAs can be carried out by those skilled in the art using conventional means. A genomic DNA can be prepared by, for example, extracting a genomic DNA from *Saccharomyces*, preparing a genomic library (examples of vectors available include plasmids, phages, cosmids, BAC, and PAC), developing this, and performing colony hybridization or plaque hybridization using a probe prepared based on the nucleotide sequence of the FDC gene (for example, the nucleotide sequence set forth in SEQ ID NO: 1). It is also possible to prepare a primer specific to the FDC gene and perform PCR using the same. In addition, a cDNA can be prepared by, for example, synthesizing a cDNA based on the mRNA extracted from *Saccharomyces*, inserting it into a vector such as λZAP to prepare a cDNA library, developing this, and performing colony hybridization or plaque hybridization in the same manner as above, or performing PCR. Then, those skilled in the art can introduce a mutation that substitutes an amino acid at position 398 of the amino acid sequence set forth in SEQ ID NO: 2 or corresponding to the position with glutamine or the like into the DNA thus prepared by using a known site-specific mutation introduction method. Examples of the site-specific mutation introduction method include the Kunkel method (Kunkel, T. A., Proc Natl Acad Sci USA, 1985, Vol. 82, Issue 2, pp. 488 to 492) and the SOE (spicing-by-overlap-extension)-PCR method (Ho, S. N., Hunt, H. D., Horton, R. M., Pullen, J. K., and Pease, L. R., Gene, 1989, Vol. 77, pp. 51 to 59). Further, those skilled in the art can artificially design a nucleotide sequence encoding a protein in which the amino acid at position 398 of FDC or corresponding to the position is substituted with glutamine or the like, and chemically synthesize the DNA of the present invention using an automated nucleic acid synthesizer based on the sequence information.

Furthermore, from the viewpoint of further improving the expression efficiency of the encoded FDC mutant in the host cell, the DNA of the present invent ion may also take the form of a DNA encoding an FDC mutant of the present invention in which codons are optimized according to the type of the host cell.

Further, the present invention can take the form of the vector inserted with the DNA so that the above-mentioned DNA can be replicated in the host cell. In the present invention, the "vector" can be constructed based on a self-replicating vector, that is, an extrachromosomal independent entity whose replication does not depend on chromosomal replication, for example, a plasmid. The vector may also be one that, when introduced into a host cell, integrates into the genome of the host cell and replicates together with the chromosome into which it has been integrated.

Examples of such a vector include a plasmid and phage DNA. Further, examples of the plasmid include plasmids derived from *Escherichia coli* (such as PET22, pBR322, pBR325, pUC118, pUC119, PUC18, and pUC19), plasmids derived from yeast (such as YEp13, YEp24, and YCp50), and plasmids derived from *Bacillus subtilis* (such as pUB110 and pTP5). Examples of the phage DNA include λ phages (such as Charon 4A, Charon 21A, EMBL3, EMBL4, λgt10, λgt11, and λZAP). Further, an insect virus vector such as baculovirus if the host cell is derived from an insect, T-DNA or the like if derived from a plant, and a retrovirus or an adenovirus vector if derived from an animal can also be used as the vector of the present invention. Further, as the procedure and method for constructing the vector of the present invention, those commonly used in the field of genetic engineering can be used. For example, in order to insert the DNA of the present invention into a vector, one employs a method or the like in which a purified DNA is first cleaved with an appropriate restriction enzyme, inserted into the restriction enzyme site or multicloning site of an appropriate vector, and ligated to the vector.

Further, the vector of the present invention may be in the form of an expression vector containing the FDC mutant encoded by the DNA in a state capable of being expressed in the host cell. In order to introduce the "expression vector" into a host cell to express the FDC mutant of the invention, it desirably contains, in addition to the aforementioned DNA, a DNA sequence to control its expression, a genetic marker to select the transformed host cell, and the like. The DNA sequence that controls expression includes a promoter, an enhancer, a splicing signal, a poly A addition signal, a ribosome binding sequence (SD sequence), a terminator, and the like. The promoter is not particularly limited as long as it exhibits transcriptional activity in the host cell, and can be obtained as a DNA sequence that controls the expression of a gene encoding a protein of the same species or heterologous to the host cell. In addition to the DNA sequence that controls the expression, a DNA sequence that induces the expression may be included. Examples of the DNA sequence that induces such expression include, when the host cell is a bacterium, a lactose operon that can induce the expression of a gene located downstream by the addition of isopropyl-β-D-thiogalactopyranoside (IPTG). The gene marker in the present invention may be appropriately selected depending on the method for selecting the transformed host cell, and for example, a gene encoding drug resistance or a gene complementing auxotrophy can be used.

Moreover, the DNA or vector of the present invention may be used by mixing with different components. The different components are not particularly limited, and examples thereof include sterile water, physiological saline, vegetable oils, surfactants, lipids, solubilizer, buffers, DNase inhibitors, and preservatives.

<Host Cell Introduced with DNA and the Like of the Present Invention>

The host cell introduced with the DNA or vector of the present invention will be described. By using a host cell transformed by the introduction of the above-mentioned DNA or vector, it becomes possible to produce the FDC mutant of the present invention, and it becomes also possible to produce an unsaturated hydrocarbon compound represented by the formula (2) or (5), or a geometric isomer thereof.

The host cell introduced with the DNA or vector of the present invention is not particularly limited, and examples thereof include microorganisms (such as *Escherichia coli*, budding yeast, fission yeast, hay bacillus, ray fungi, and filamentous fungi), plant cells, insect cells, and animal cels, and from the viewpoint of showing high proliferation property in a short time with a relatively inexpensive medium, and contributing to the production of unsaturated hydrocarbon compounds represented by the formula (2) or (5), or geometric isomers thereof, which are highly productive, it is preferable to use a microorganism as a host cell, and it is more preferable to use *Escherichia coli.*

Further, from the viewpoint of inducing prenylation of flavin mononucleotide (FMN) and producing prFMN or an isomer thereof that contributes to the productivity improvement of the unsaturated hydrocarbon compounds represented by the formula (2) or (5), or geometric isomers thereof, the host cell introduced with the DNA or vector or the present invention is preferably a cell carrying flavin prenyltransferase.

Further, in the production of butadiene, from the viewpoint that muconic acid, which is a substrate of the FDC mutant of the present invention, can be easily produced from glucose as a raw material, the host cell introduced with the DNA or vector of the present invention is preferably a cell in which the pathway for biosynthesizing muconic acid from glucose via 3-dehydroshikimic acid and catechol is activated. Examples of such cells include cells with enzymes that suppress the activity of phosphotransferase-based enzymes and pyruvate kinases and allow the synthesis of aromatic compounds from chorismic acid or isochorismic acid (for example, microorganisms described in International Publication No. 2017/033965) and *Escherichia coli, Pseudomonas putida*, or budding yeast described in Kruyer N S et al., Curr Opin Biotechnol. 2017, June; 45: pp. 136 to 143.

The introduction of the DNA or vector of the present invention can also be carried out according to the methods commonly used in the art. For example, examples of the method for introducing into a microorganism such as *Escherichia coli* include a heat shock method, an electroporation method, a spheroplast method, and a lithium acetate method, examples of the method for introducing into plant cells include a method using *Agrobacterium* and a particle gun method, examples of the method for introducing into insect cells include a method using baculovirus and an electroporation method, and examples of the method for introducing into animal cells include a calcium phosphate method, a lipofection method, and an electroporation method.

The DNA and the like introduced into the host cell in this manner may be retained in the host cell by being randomly inserted into the genomic DNA, may be retained by homologous recombination, and if it is a vector, it can be replicated and retained as an independent entity outside the genomic DNA.

Further, in the host cell introduced with the DNA or vector according to the present invention, the catalytic activity for producing butadiene measured by the method shown in Examples described later is preferably 30 μM or more (for example, 40 μM or more, 50 μM or more, 60 μM or more, 70 μM or more, 80 μM or more, and 90 μM or more), more preferably 100 μM or more (for example, 200 μM or more, 300 μM or more, and 400 μM or more), further preferably 500 μM or more (for example, 600 μM or more, 700 μM or more, 800 μM or more, and 900 μM or more), more preferably 1 mM or more (for example, 1.5 mM or more, 2 mM or more, and 2.5 mM or more), and particularly preferably 3 mM or more.

<Method 1 for Producing Unsaturated Hydrocarbon Compound>

As mentioned above, the FDC mutant of the present invention has a catalytic activity for producing unsaturated hydrocarbon compounds. Therefore, provided is a method for producing an unsaturated hydrocarbon compound represented by the following formula (2) or (5) or a geometric isomer thereof, including the steps of decarboxylating an unsaturated hydrocarbon dicarboxylic acid compound represented by the following formula (1) or (3) or a geometric isomer thereof in the presence of the FDC mutant of the present invention.

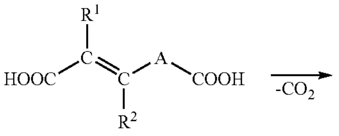

(1)

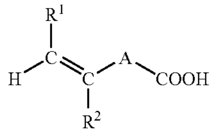

(2)

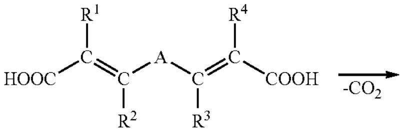

(3)

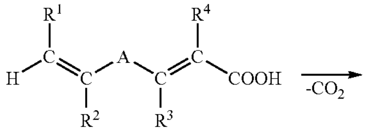

(4)

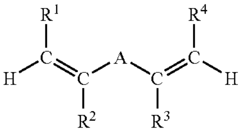

(5)

In the present invention, the "unsaturated hydrocarbon compound or a geometric isomer thereof" produced by the reaction means, as shown in the formulas (2) and (5), a hydrocarbon compound having at least one carbon-carbon double bond, or may have a linear or branched alkyl croup having 1 to carbon atoms, a linear or branched alkoxy group having 1 to 5 carbon atoms, or a hydroxyl group introduced therein. Examples of such a compound include butadiene (1,3-butadiene), 2,4-pentadiene acid, isocrotonic acid, 3-methylisocrotonic acid, 3-pentenoic acid, and 10-undecenoic acid.

In the present invention, the "unsaturated hydrocarbon dicarboxylic acid compound or a geometric isomer thereof," which is a raw material for producing an unsaturated hydrocarbon compound, means, as shown in the above formulas (1) and (3), a hydrocarbon compound having at least one carbon-carbon double bond and at least two carboxyl groups, or may have a linear or branched alkyl group having 1 to 5 carbon atoms, a linear or branched alkoxy group having 1 to 5 carbon atoms, or a hydroxyl group introduced therein. Examples of such a compound include cis,cis-muconic acid, cis,trans-muconic acid, trans,trans-muconic acid, glutaconic acid, 2-methylglutaconic acid, 3-methylglutaconic acid, and traumatic acid.

Such compounds represented by the formulas (1) and (3) and geometric isomers thereof can be purchased as commercially available products as shown in Examples described later. Further, those skilled in the art can also synthesize by appropriately referring to a known synthesis method (for example, the method described in Kiyoshi Kudo et al., Journal of the Japan Petroleum institute, published on Jul. 13, 1994, Vol. 38, Issue 1, pp. 48 to 51).

The "$R^1$" and "$R^2$" in the compounds represented by the formulas (1) and (2) and geometric isomers thereof, or the "$R^1$," "$R^2$," "$R^3$," and "$R^4$" in the compounds represented by the formulas (3) to (5) and geometric isomers thereof each independently represent a hydrogen atom, a linear or branched alkyl group having 1 to 5 carbon atoms, a linear or branched alkoxy group having 1 to 5 carbon atoms, or a hydroxyl group.

Examples of the "linear or branched alkyl group having to 5 carbon atoms" include a methyl group, an ethyl group, an n-propyl group, an i-propyl group, an n-butyl group, an i-butyl group, an s-butyl group, a t-butyl group, an n-pentyl group, and an i-pentyl group.

Examples of the "linear or branched alkoxy group having 1 to 5 carbon atoms" include a methoxy group, an ethoxy group, an n-propoxy group, an i-propoxy group, an n-butoxy group, an i-butoxy group, an s-butoxy group, a t-butoxy group, an n-pentyloxy group, an i-pentyloxy group, an n-pentyloxy group, and a 1,2-dimethyl-propoxy group.

Further, "A" in the compounds represented by the formulas (1) to (5) and geometric isomers thereof represents an optionally substituted linear hydrocarbon group having 0 to 5 carbon atoms. Note that the an "optionally substituted linear hydrocarbon group having 0 carbon atoms" means that the carbon atoms bonded via "A" are directly bonded to each other without via "A" in the compounds represented by the formulas (1) to (5) and geometric isomers thereof. Further, when the optionally substituted linear hydrocarbon group has 2 to 5 carbon atoms, at least one double bond may be formed between adjacent carbon atoms. Further, examples of the substituent that the hydrocarbon group may have in "A" include a linear or branched alkyl group having 1 to 5 carbon atoms, a linear or branched alkoxy group having 1 to 5 carbon atoms, a hydroxyl group, a halogen atom (such as fluorine, chlorine, bromine, or iodine), a nitro group, a cyano group, an amino group, a carboxyl group, and a formyl group.

The conditions for decarboxylating the unsaturated hydrocarbon dicarboxylic acid compound in the presence of the FDC mutant of the present invention may be any conditions that promotes the decarboxylation and produces the unsaturated hydrocarbon compound, and those skilled in the art can appropriately adjust and set the composition of the reaction solution, the pH of the reaction solution, the reaction temperature, the reaction time, and the like.

For example, the reaction solution added with the FDC mutant of the present invention and a substrate thereof, the unsaturated hydrocarbon dicarboxylic acid compound, is not particularly limited as long as the reaction is not hindered, and is preferably a buffer solution having a pH of 6 to 8, and more preferably a buffer solution containing potassium chloride and sodium phosphate having a pH of 6 to 7. Further, from the viewpoint of more facilitating the reaction, it is preferable to contain a prenylated flavin mononucleotide (prFMN) or an isomer thereof ($prFMN^{ketimine}$ or $prFMN^{iminiu}$, and for these prFMN and isomers thereof, refer to NPL 1).

Further, as the FDC mutant of the present invention used in such a reaction, it is possible to use only one kind of FDC derived from *Saccharomyces* in which the amino acid at position 398 of the amino acid sequence set forth in SEQ ID NO: 2 or corresponding to the position is substituted with glutamine or the like, but two or more kinds of the FDC mutant of the present invention can also be used in combination. Further, as shown in PTL 3, from the viewpoint of more facilitating decarboxylation of the unsaturated hydrocarbon carboxylic acid compound, a ferulic acid decarboxylase is preferably used in combination in which the amino acid at position 398 of the amino acid sequence set forth in SEQ ID NO: 2 or corresponding to the position is threonine.

In addition, the reaction temperature is not particularly limited as long as it does not hinder the reaction, but is usually 20 to 40° C., and preferably 25 to 37° C. Further, the reaction time may be any time as long as the unsaturated hydrocarbon compound can be produced, and is not particularly limited, but is usually 30 minutes to 7 days, and preferably 12 hours to 2 days.

Further, since the unsaturated hydrocarbon compound produced under such conditions is generally easily vaporized, it can be collected by a known collection and purification method for volatile gas. Examples of such a collecting method include gas stripping, fractional distillation, adsorption, desorption, pervaporation, desorption of isoprene adsorbed on the solid phase from the solid phase by heat or vacuum, extraction with a solvent, or chromatography (such as gas chromatography). Further, even when the produced olefin compound is a liquid, it can also be collected by appropriately using a known collection and purification method (such as distillation or chromatography). Further, these methods may be carried out alone or may be carried out in combination as appropriate in multiple steps.

<Method 2 for Producing Unsaturated Hydrocarbon Compound>

As mentioned above, by culturing a host cell transformed to express the FDC mutant of the present invention, an unsaturated hydrocarbon compound can be produced with high productivity. Therefore, the present invention also provides a method for producing an unsaturated hydrocarbon compound, including the steps of culturing the host cell introduced with a DNA or vector encoding the FDC mutant of the present invention; and collecting an unsaturated hydrocarbon compound represented by the formula (2) or (5) or a geometric isomer thereof produced in the host cell and/or a culture product thereof.

The "host cell introduced with a DNA or vector encoding the FDC mutant of the present invention" is as described above, and the FDC mutant of the present invention expressed in such a host cell may be only one kind of *Saccharomyces*-derived FDC in which the amino acid at position 398 of the amino acid sequence set forth in SEQ ID NO: 2 or corresponding to the position is substituted with glutamine or the like, but may be two or more kinds of the FDC mutant of the present invention. Further, as shown in PTL 3, from the viewpoint of more facilitating decarboxylation of the unsaturated hydrocarbon carboxylic acid compound, it is preferable that in the host cell, a ferulic acid decarboxylase is also expressed in which the amino acid at position 398 of the amino acid sequence set forth in SEQ ID NO: 2 or corresponding to the position is threonine.

The cell culture conditions are as described below, and it is preferable that the medium is added with the unsaturated hydrocarbon dicarboxylic acid compound represented by the formula (1) or (3), which is the substrate of the decarboxylase according to the present invention, or a geometric isomer thereof. The culture temperature may be appropriately changed in design according to the type of host cell: used, but is usually 20 to 40° C., and preferably 25 to 37° C.

In the present invention, "culture product" refers to a medium containing proliferated host cells, secretory products of the host cells, and metabolic products of the host cells, and the like obtained by culturing host cells in the medium, and includes dilutions and concentrates thereof.

The collection of unsaturated hydrocarbon compounds from such host cells and/or culture products is also not particularly limited, and can be carried out by using the above-mentioned known collection and purification methods. Further, the timing of collection may be any time as long as it is appropriately adjusted according to the type of host cells to be used and an unsaturated hydrocarbon compound can be produced, and is usually 30 minutes to 7 days, and preferably 12 hours to 2 days.

<Agent for Promoting Production of Unsaturated Hydrocarbon Compound>

As described above, by using the FDC mutant of the present invention, the DNA encoding the FDC mutant, or the vector inserted with the DNA, it is possible to decarboxylate an unsaturated hydrocarbon dicarboxylic acid compound represented by the formula (1) or (3) or a geometric isomer thereof, and promote the formation of unsaturated hydrocarbon compounds represented by the formula (2) or (5) or their geometric isomers.

Therefore, the present invention provides an agent for decarboxylating an unsaturated hydrocarbon dicarboxylic acid compound represented by the formula (1) or a geometric isomer thereof and promoting production of an unsaturated hydrocarbon compound represented by the formula (2) or a geometric isomer thereof, or an agent for decarboxylating the unsaturated hydrocarbon dicarboxylic acid compound represented by the formula (3) or a geometric isomer thereof and promoting the production of the unsaturated hydrocarbon compound represented by the formula (5) or a geometric isomer thereof, including the FDC mutant of the present invention, the DNA encoding the FDC mutant, or the vector inserted with the DNA.

Such an agent may be any one containing the FDC mutant of the present invention or the like, or may be used in mixture with different components. The different components are not particularly limited, and examples thereof include sterile water, physiological saline, vegetable oils, surfactants, lipids, solubilizer, buffers, protease inhibitors, DNase inhibitors, and preservatives.

The present invention can also provide a kit containing such an agent. In the kit of the present invention, the agent may be contained in the form of the host cell transformed due to the introduction of the DNA and the like of the present invention. Further, the kit of the present invention may contain, in addition to such an agent, the compound represented by the above formula (1) or (3) or a geometric isomer thereof, a host cell for introducing DNA and the like according to the present invention, a medium for culturing the host cell, an instruction manual for their use, and the like. Further, such a usage instruction manual is an instruction manual for using the agent of the present invention or The like in the above-mentioned method for producing an unsaturated hydrocarbon compound. The instruction manual may include, for example, information about the experimental methods and experimental conditions for the production method of the present invention, the agent of the present invention, and the like (including information such as a vector map showing the nucleotide sequence of a vector and the like, sequence information on an FDC mutant of the present invention, origin and properties of the host cell, and information on culture conditions of the host cell and the like).

<Method for Producing FDC Mutant of the Present Invention>

As shown in Examples described later, by culturing a host cell introduced with a DNA and the like encoding the FDC mutant of the present invention, it is possible to produce the FDC mutant in the host cell.

Therefore, the present invention can also provide a method for producing an FDC mutant of the present invention, including the steps of culturing the host cell introduced with a DNA encoding the FDC mutant of the present invention or a vector including the DNA; and collecting a protein expressed in the host cell.

In the present invention, the condition of "culturing a host cell" may be any condition as long as the host cell can produce the FDC mutant of the present invention, and those skilled in the art can appropriately adjust and set the temperature, the presence or absence of addition of air, the concentration of oxygen, the concentration of carbon dioxide, the pH of the medium, the culture temperature, the culture time, the humidity, and the like according to the type of the host cell, medium used, and the like.

Such medium may contain anything that can be assimilated by the host cell, and examples of its content include carbon source, nitrogen source, sulfur source, inorganic salts, metal, peptone, yeast extract, meat extract, casein hydrolyzate, serum, and the like. Further, for example, such a medium may be added with IPTG for inducing the expression of the DNA encoding the FDC mutant of the present invention, an antibiotic (such as ampicillin) corresponding to the drug resistance gene that can be encoded by the vector of the present invention, or a nutrient (such as arginine or histidine) corresponding to the gene that complements the auxotrophy that can be encoded by the vector of the invention.

Then, examples of the method for "collecting a protein expressed in the cell" from the host cell cultured in this way include a method in which the host cells are collected from the medium by filtration, centrifugation, or the like, and the collected host cells are treated by cytolysis, grinding treatment, pressure crushing, or the like, and further, the protein expressed in the host cell purified and concentrated by ultrafiltration treatment, salting out, solvent precipitation such as ammonium sulfate precipitation, chromatography (such as gel chromatography, ion exchange chromatography, or affinity chromatography), or the like. Further, when the above-mentioned purified tagged protein is added to the FDC mutant of the present invention, it can be purified and collected using a substrate to which the tagged protein is adsorbed. Further, these purification and concentration methods may be carried out alone or may be carried out in combination as appropriate in multiple steps.

Further, the FDC mutant or the present invention is not limited to the above biological synthesis, and can also be produced by using the DNA and the like of the present invention and a cell-free protein synthesis system. The cell-free protein synthesis system is not particularly limited, and examples thereof include wheat germ-derived, *Escherichia coli*-derived, rabbit reticulocyte-derived, and insect cell-derived synthetic Systems. Further, those skilled in the art can chemically synthesize the FDC mutant of the present invention using a commercially available peptide synthesizer or the like.

Further, the present invention can also provide a method for producing a ferulic acid decarboxylase mutant having enhanced catalytic activity for producing an unsaturated hydrocarbon compound represented by the formula (2) or (5) or a geometric isomer thereof, including the steps of substituting, in a ferulic acid decarboxylase derived from *Saccharomyces*, an amino acid at position 398 of an amino acid sequence set forth in SEQ ID NO: 2 or corresponding to the position with glutamine or the like, and preferably further substituting an amino acid at a different position (such as the above-mentioned amino acid at position 397 of the amino acid sequence set forth in SEQ ID NO: 2 or corresponding to the position).

The "ferulic acid decarboxylase having enhanced catalytic activity for producing an unsaturated hydrocarbon compound represented by the formula (2) or (5) or a geometric isomer thereof" means an FDC having a higher catalytic activity for producing unsaturated hydrocarbon compounds after introducing a mutation into the amino acid at position 398 of the amino acid sequence set fort in SEQ ID NO: 2 or corresponding to the position, preferably by further introducing a mutation into the amino acid at the above different position, and the comparison target is usually the wild-type FDC derived from *Saccharomyces* described above.

Note that for a preferred embodiment of the mutation introduced into the amino acid at position 398 of the amino acid sequence set forth in SEQ ID NO: 2 or corresponding to the position, or the amino acid at a different position (such as the amino acid at position 397 of the amino acid sequence set forth in SEQ ID NO: 2 or corresponding to the position), that is, substitution with glutamine or the like or histidine or the like, refer to the above description of <Decarboxylase According to the Present Invention>.

The "substitution with glutamine or the like or histidine or the like" in FDC can be carried out by modifying the encoding DNA. As described above, "modification of DNA" can be appropriately carried out by a method known to those skilled in the art, for example, a site-directed mutagenesis method or a method for chemically synthesizing DNA based on modified sequence information. Further, "substitution with glutamine or the like or histidine or the like" can also be carried out by using a method for chemically synthesizing a peptide as described above. Further, as described above, whether or not the catalytic activity for producing unsaturated hydrocarbon compounds IS enhanced by the introduction of such a mutation can be evaluated by GC-MS analysis or the like.

EXAMPLES

Hereinafter, the present invention will be described in more detail based on Examples, but the present invention is not limited to the following Examples.

Example 1

As shown in PTL 3, the present inventors have found that the introduction of a mutation accompanied by an amino acid substitution into ferulic acid decarboxylase (FDC)

derived from *Aspergillus* enhances the catalytic activity for the production of butadiene using muconic acid as a substrate.

This time, in order to select a more suitable FDC, the catalytic activity of FDCs derived from various microorganisms was analyzed by the method shown below.

<Preparation of Plasmid Vector>

First, in order to efficiently express FDCs derived from various microorganisms in *Escherichia coli*, the C-terminal of the wild-type nucleotide sequence encoding them was modified by fusing a polyhistidine tag in consideration of the frequency of codon use in *Escherichia coli* (the nucleotide sequence after the sequence modification is set forth in SEQ ID NO: 3).

Next, the DNA composed of such a modified nucleotide sequence was chemically synthesized according to a conventional method. Then, the DNA thus prepared and pET22b (+) vectors (manufactured by Novagen) were ligated by the Gibson Assembly method (using a New England Biolabs kit NEBuilder HiFi DNA Assembly Master Mix (registered trademark)) to prepare plasmid vectors (FDC vectors) capable of expressing the various wild-type FDCs in *Escherichia coli*. Similarly, the DNA obtained by amplifying a gene (SEQ ID NO: 6) encoding flavin prenyltransferase (hereinafter also referred to as "UbiX") from an *Escherichia coli* (K-12) strain by the Polymerase Chain Reaction method and pColADuet vectors (manufactured by Novagen) were ligated by the Gibson Assembly method to prepare plasmid vectors (UbiX vectors) capable of expressing the wild-type UbiX in *Escherichia coli.*

<Preparation of Enzyme Reaction Solution and Measurement of Enzymatic Activity>

The vectors prepared as described above (5 μg of the FDC vectors and 5 μg of the UbiX vectors) were introduced into *Escherichia coli* C41 (DE3) strain (manufactured by Lucigen Corporation, 100 μL) by the heat shock method to prepare transformants co-expressing wild-type FDC and UbiX.

Then, each of these transformants was cultured in LB medium supplemented with ampicillin and kanamycin for 6 hours. Note that by this culturing for 6 hours (preculture), the proliferation of these transformants had reached a plateau. Therefore, the quantity of cells at the start of the enzyme reaction described later became uniform among these transformants.

Further, to 12 g/L tryptone, 24 g/L yeast extract, 10 g/L glycerol, 9.4 g/L dipotassium hydrogen phosphate, 2.2 g/L potassium dihydrogen phosphate, 20 g/L lactose, 100 mg/L ampicillin, and 50 mg/L kanamycin, cis,cis-muconic acid (manufactured by Sigma-Aldrich), which is a substrate, was added to a final concentration of 0.5 mM to prepare a medium for enzyme reaction.

Then, to a 10 mL vial for a headspace gas chromatography-mass spectrometer (HS/GSMS), 100 μL of the *Escherichia coli* culture medium cultured for 6 hours and 2.5 mL of the medium for enzyme reaction were added, and immediately after that, the cap of the vial was closed, and culture was further carried out at 37° C. and a shaking speed of 180 rpm. The peak area representing the amount of butadiene (1,3-butadiene) produced in the headspace of the vial 18 hours after the start of the culture was measured by GC-MS (product name: GCMS-QP Ultra, manufactured by Shimadzu Corporation). Then, based on the obtained measured values, the amount of butadiene produced in FDCs derived from various microorganisms was compared with that in FDCs derived from *Aspergillus*.

As a result, although not shown in the drawings or tables, in FDCs derived from *Debaryomyces hansenii* (Uniprot ID: Q6BJQ8), for example, about 0.2 times the activity was detected as compared with those derived from *Aspergillus*, and in FDCs derived from *Colletotrichum chlorophyte* (Uniprot ID: A0A0A3FMK0), about 4 times the activity was detected as compared with those derived from *Aspergillus*. Among them, in FDCs derived from *Saccharomyces cerevisiae* (amino acid sequence set forth in SEQ ID NO: 2), an activity (amount of butadiene produced: 24.5 μM) orders of magnitude higher (about 19.6 times) was detected as compared with that derived from *Aspergillus.*

Example 2

As shown in Example 1, high butadiene production catalytic activity was observed in the wild-type FDC derived from *Saccharomyces cerevisiae*. Thus, in order to further improve this high catalytic activity, a mutation was introduce in a wild-type FDC derived from *Saccharomyces cerevisiae*, in which isoleucine at position 398 and/or phenylalanine at position 397 is each substituted with another amino acid, as in PTL 3. Note that position 398 and position 397 of the *Saccharomyces cerevisiae*-derived FDC correspond to position 395 and position 394 of the *Aspergillus*-derived FDC, respectively (see PTL 3). Then, the catalytic activity of the obtained mutant introducer was evaluated.

Specifically, a primer encoding the amino acid sequence introduced with each mutation was designed and synthesized. Then, the primer was used with the vector encoding the wild-type FDC derived from *Saccharomyces cerevisiae* prepared in Example 1 as a template, and according to the Gibson Assembly method protocol, by fusing the FDC introduced with each mutation with a polyhistidine tag at the C-terminal, plasmid vectors (modified FDC vectors) that could be expressed in *Escherichia coli* were prepared. Then, n the above <Preparation of Enzyme Reaction Solution and Measurement of Enzymatic Activity>, a modified FDC vector was introduced instead of the wild-type FDC vector, a transformant was prepared, and the enzymatic actvity was measured. Table 7 presents the obtained results.

TABLE 7

| | | Position 398 | | | | | | |
|---|---|---|---|---|---|---|---|---|
| | | I | T | H | Q | N | M | F |
| Position 397 | F | 1.0 | 3.5 | 5.1 | 9.3 | 8.8 | 16.4 | 6.8 |
| | Y | 1.7 | 1.1 | 6.3 | 19.3 | 3.6 | 16.2 | 9.0 |
| | L | 0.6 | 1.1 | 1.8 | 16.9 | 5.4 | 13.2 | 4.8 |
| | M | 1.6 | 2.0 | 1.6 | 33.8 | 8.9 | 18.3 | 3.0 |
| | W | 2.3 | 2.4 | 3.4 | 8.8 | 17.1 | 10.8 | 6.0 |
| | H | 3.8 | 4.8 | 13.0 | 75.1 | 21.7 | 37.3 | 14.8 |

As is clear from the results presented Table 7, it was clarified that substitution of isoleucine at position 398 of the *Saccharomyces cerevisiae*-derived FDC with another amino acid (glutamine, methionine, asparagine, phenylalanine, histidine, or threonine) generally improved the catalytic activity for the production of butadiene (improved the catalytic activity at least about 3 times as compared with the wild-type FDC before the mutation introduction). In particular, the FDC mutant in which the aforementioned position was substituted with glutamine and the FDC mutant in which the aforementioned position was substituted with methionine had their catalytic activities improved 9.3 times and 16.4 times, respectively.

Furthermore, as presented in Table 7, it was also clarified that substitution of position 397 with another amino acid in addition to the amino acid substitution at position 398 could further improve the catalytic activity. In particular, in the mutant in which position 398 was substituted with glutamine, when position 397 was substituted with histidine or methionine, the catalytic activity was improved 75.1 times and 33.8 times, respectively, as compared with the wild-type FDC. Further, in the mutant on which position 398 was substituted with methionine, when position 397 was substituted with histidine, the catalytic activity was improved 37.3 times as compared with the wild-type FDC.

Note that in the mutant in which position 397 was substituted with histidine and position 398 was substituted with glutamine, the amount of butadiene produced when the concentration of the substrate (muconic acid) was 10 times (5.0 mM) was 2.07 mM.

Example 3

In Example 2, in the double mutants (F397H/I398Q, F397M/I398Q, and F397H/I398M) in which improvement in catalytic activity was particularly observed, amino acids at various positions were substituted with other amino acids to prepare triple mutants, and their enzymatic activities were evaluated.

As a result, it was clarified that substitution of the amino acid at position 286, 334, or 440 with another amino acid further improved the catalytic activity. For example, in F397H/I398Q, the catalytic activity was improved as compared with that before the mutation introduction, by 1.2 times by substitution of isoleucine at position 189 with methionine, by 1.5 times by substitution of methionine at position 286 with leucine, by 1.1 times by substitution of threonine at position 326 with leucine, and by 1.5 times by substitution of valine at position 326 with isoleucine. Further, in F397M/I398Q and F397H/I398M, the catalytic activity was improved as compared with that before the mutation introduction, by 1.1 times by substitution of valine at position 334 with isoleucine.

INDUSTRIAL APPLICABILITY

As described above, according to the present invention, it is possible to provide an enzyme capable or producing an unsaturated hydrocarbon compound such as butadiene with high productivity, and a method for producing an unsaturated hydrocarbon compound using the enzyme. Further, according to the present invention, it is possible to produce an unsaturated hydrocarbon compound by biosynthesis without using chemical synthesis, so that the burden on the environment is small. Therefore, the present invention is extremely useful in the production of raw materials for various synthetic polymers such as synthetic rubbers including butadiene.

The invention claimed is:

1. A method for producing an unsaturated hydrocarbon compound with the following formula (2) or a geometric isomer thereof, the method comprising:

decarboxylating an unsaturated hydrocarbon dicarboxylic acid compound with the following formula (1) or a geometric isomer thereof in the presence of a ferulic acid decarboxylase

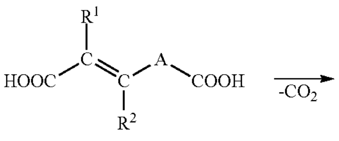

(1)

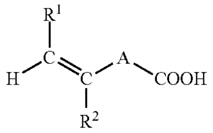

(2)

wherein in formula (1) and (2),

"$R^1$" and "$R^2$" each independently is a hydrogen atom, a linear or branched alkyl group having 1 to 5 carbon atoms, a linear or branched alkoxy group having 1 to 5 carbon atoms, or a hydroxyl group; and "A" is an optionally substituted linear hydrocarbon group having 0 to 5 carbon atoms, wherein when the number of carbon atoms is 2 to 5, a double bond may be formed between adjacent carbon atoms, wherein the ferulic acid decarboxylase is derived from *Saccharomyces cerevisiae* and comprises a substitution of an amino acid at position 398 of the amino acid sequence set forth in SEQ ID NO: 2 or a corresponding position with glutamine, methionine, asparagine, phenylalanine, histidine, or threonine, and wherein the ferulic acid decarboxylase has a catalytic activity for producing the unsaturated hydrocarbon compound with formula (2) or the geometric isomer thereof that is 19.6 times or more a catalytic activity of wild-type ferulic acid decarboxylase derived from *Aspergillus* for producing the unsaturated hydrocarbon compound with formula (2) or the geometric isomer thereof.

2. A method for producing an unsaturated hydrocarbon compound with the following formula (5) or a geometric isomer thereof, the method comprising:

decarboxylating an unsaturated hydrocarbon dicarboxylic acid compound with the following formula (3) or a geometric isomer thereof in the presence of a ferulic acid decarboxylase

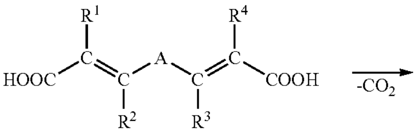

(3)

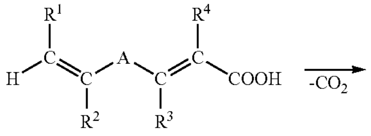

(4)

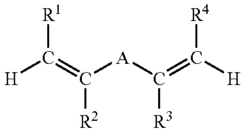

(5)

wherein in formula (3) to (5),

"$R^1$," "$R^2$," "$R^3$," and "$R^4$" each independently is a hydrogen atom, a linear or branched alkyl group having 1 to 5 carbon atoms, a linear or branched alkoxy group having 1 to 5 carbon atoms, or a hydroxyl group; and "A" is an optionally substituted linear hydrocarbon group having 0 to 5 carbon atoms, wherein when the number of carbon atoms is 2 to 5, a double bond may be formed between adjacent carbon atoms, wherein ferulic acid decarboxylase is derived from *Saccharomyces cerevisiae* and comprises a substitution of an amino acid at position 398 of the amino acid sequence set forth in SEQ ID NO: 2 or a corresponding position with glutamine, methionine, asparagine, phenylalanine, histidine, or threonine, and wherein the ferulic acid decarboxylase has a catalytic activity for producing the unsaturated hydrocarbon compound with formula (5) or the geometric isomer thereof that is 19.6 times or more a catalytic activity of wild-type ferulic acid decarboxylase derived from *Aspergillus* for producing the unsaturated hydrocarbon compound with formula (5) or the geometric isomer thereof.

3. A method for producing an unsaturated hydrocarbon compound, the method comprising:

culturing a host cell introduced with a DNA encoding a ferulic acid decarboxylase or a vector comprising the DNA; and collecting an unsaturated hydrocarbon compound with the following formula (2) or (5) or a geometric isomer thereof produced in the host cell and/or a culture product thereof (2)

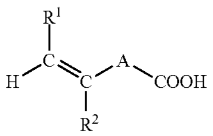

(5)

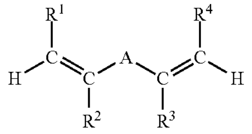

wherein in formulas (2) and (5),

"$R^1$," "$R^2$," "$R^3$," and "$R^4$" each independently is a hydrogen atom, a linear or branched alkyl group having 1 to 5 carbon atoms, a linear or branched alkoxy group having 1 to 5 carbon atoms, or a hydroxyl group; and "A" is an optionally substituted linear hydrocarbon group having 0 to 5 carbon atoms, wherein when the number of carbon atoms is 2 to 5, a double bond may be formed between adjacent carbon atoms, wherein the ferulic acid decarboxylase is derived from *Saccharomyces cerevisiae* and comprises a substitution of an amino acid at position 398 of the amino acid sequence set forth in SEQ ID NO: 2 or a corresponding position with glutamine, methionine, asparagine, phenylalanine, histidine, or threonine, and wherein the ferulic acid decarboxylase has a catalytic activity for producing the unsaturated hydrocarbon compound with formula (2) or (5) or the geometric isomer thereof that is 19.6 times or more a catalytic activity of wild-type ferulic acid decarboxylase derived from *Aspergillus* for producing the unsaturated hydrocarbon compound with formula (2) or (5) or the geometric isomer thereof.

4. The method according to claim 1, wherein the catalytic activity of the ferulic acid decarboxylase for producing the unsaturated hydrocarbon compound with formula (2) or the geometric isomer thereof is 30 times or more the catalytic activity of wild-type ferulic acid decarboxylase derived from *Aspergillus* for producing the unsaturated hydrocarbon compound with formula (2) or the geometric isomer thereof.

5. The method according to claim 2, wherein the catalytic activity of the ferulic acid decarboxylase for producing the unsaturated hydrocarbon compound with formula (5) or the geometric isomer thereof is 30 times or more the catalytic activity of wild-type ferulic acid decarboxylase derived from *Aspergillus* for producing the unsaturated hydrocarbon compound with formula (5) or the geometric isomer thereof.

6. The method according to claim 3, wherein the catalytic activity of the ferulic acid decarboxylase for producing the unsaturated hydrocarbon compound with formula (2) or (5) or the geometric isomer thereof is 30 times or more the catalytic activity of wild-type ferulic acid decarboxylase derived from *Aspergillus* for producing the unsaturated hydrocarbon compound with formula (2) or (5) or the geometric isomer thereof.

* * * * *